United States Patent [19]

Sanczuk et al.

[11] 4,198,411

[45] Apr. 15, 1980

[54] N-ARYL-N-(1-L-4-PIPERIDINYL)-ARYLACEYTAMIDES

[75] Inventors: Stefan Sanczuk, Vosselaar; Hubert K. F. Hermans, Gierle, both of Belgium

[73] Assignee: Janssen Pharmaceutica N.V., Beerse, Belgium

[21] Appl. No.: 924,531

[22] Filed: Jul. 13, 1978

Related U.S. Application Data

[60] Division of Ser. No. 795,669, May 11, 1977, Pat. No. 4,126,689, which is a continuation-in-part of Ser. No. 713,756, Aug. 12, 1976, abandoned, Division of Ser. No. 700,694, Jun. 28, 1976, abandoned, Ser. No. 700,638, Jun. 28, 1976, abandoned, Ser. No. 700,637, Jun. 28, 1976, abandoned, Ser. No. 700,636, Jun. 28, 1976, abandoned, Ser. No. 700,635, Jun. 28, 1976, abandoned, Ser. No. 700,352, Jun. 28, 1976, abandoned, and Ser. No. 700,351, Jun. 28, 1976, abandoned.

[51] Int. Cl.$^2$ .............................................. C07D 401/02
[52] U.S. Cl. ................................... 424/251; 424/263; 544/333; 544/194
[58] Field of Search ................ 424/251, 263; 544/333; 546/194

[56] References Cited

U.S. PATENT DOCUMENTS

| | | | |
|---|---|---|---|
| 2,748,134 | 5/1956 | Stoll et al. | 260/293.77 |
| 3,164,600 | 1/1965 | Janssen et al. | 260/293.67 |
| 3,869,463 | 3/1975 | Archibald | 260/293.61 |

OTHER PUBLICATIONS

CA vol. 78, (1973), 147752r.
CA vol. 77, (1972), 34349(a).

*Primary Examiner*—Nicholas S. Rizzo
*Attorney, Agent, or Firm*—Salvatore R. Conte

[57] ABSTRACT

Novel N-aryl-N-(1-L-4-piperidinyl)arylacetamides useful as antiarrhythmic agents, a method of treating arrhythmia which comprises the systemic administration of such compounds to warm-blooded animals and pharmaceutical compositions to be used therefor.

3 Claims, No Drawings

N-ARYL-N-(1-L-4-PIPERIDINYL)-ARYLACEYTA-MIDES

CROSS-REFERENCE TO RELATED APPLICATIONS

This is a division, of application Ser. No. 795,669 now U.S. Pat. No. 4,126,689, filed May 11, 1977 which in turn is a continuation-in-part of Ser. No. 713,756, filed 8/12/76 now abandoned; and our divisional applications threof: Ser. Nos. 700,351, 700,352, 700,635, 700,636, 700,637, 700,638 and 700,694, all filed June 28, 1976 and all now abandoned.

BACKGROUND OF THE INVENTION

This invention pertains to the field of N-aryl-N-(4-piperidinyl)-arylacetamides. In the prior art there may be found some N-aryl-N-(4-piperidinyl)amides having pharmacological, e.g., analgesic, properties. A number of such compounds may be found in the following references:
U.S. Pat. No. 2,748,134;
U.S. Pat. No. 3,869,463;
U.S. Pat. No. 3,164,600;
C.A., 78, 147752r (1973); and
C.A., 77, 34349a (1972).
Among other points of difference the anti-arrhythmic compounds of this invention differ from such known compounds by the nature of the arylacetamide group attached to the 4-position of the piperidine nucleus.

DESCRIPTION OF THE PREFERRED EMBODIMENTS

The N-aryl-N-(1-L-4-piperidinyl)arylacetamides with which this invention is concerned may structurally be represented by the formula:

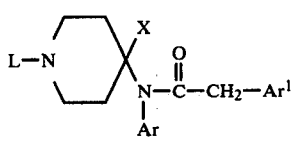

(I)

and the pharmaceutically acceptable acid addition salts thereof, wherein:
L is a member selected from the group consisting of hydrogen, alkyl having from 1 to 10 carbon atoms, cycloalkyl, cycloalkyilower alkyl and lower alkenyl;
Ar is a member selected from the group consisting of phenyl, mono- and di-substituted phenyl, pyridinyl and 2-pyrimidinyl, wherein each substituent in said mono- and di-substituted phenyl is independently selected from the group consisting of halo and lower alkyl;
$Ar^1$ is a member selected from the group consisting of phenyl, mono- and di-substituted phenyl, and thienyl, wherein each substituent in said mono- and di-substituted phenyl is independently selected from the group consisting of halo, lower alkyl, hydroxy and lower alkyloxy; and
X is a member selected from the group consisting of hydrogen, lower alkyloxycarbonyl and lower alkyloxymethyl.
More particularly, the term "alkyl" as used in the definition of L is meant to include straight and branch chained saturated hydrocarbon radicals having therein from 1 to 10 carbon atoms, such as, for example, methyl, ethyl, 1-methylethyl, propyl, 1-methylpropyl, butyl, 2-methylbutyl, 1,1-dimethylethyl, pentyl, hexyl, heptyl, decyl and the like alkyls; "lower alkyl" as used in the foregoing and in subsequent definitions refers to straight and branch chained alkyl radicals having from 1 to about 6 carbon atoms, such as, for example, methyl, ethyl, 1-methylethyl, propyl, butyl, pentyl, hexyl and the like; "lower alkenyl" refers to alkenyl radicals having from 3 to about 6 carbon atoms, such as, for example, 2-propenyl, 2-butenyl, 3-butenyl, 2-pentenyl and the like; the term "cycloalkyl" refers to cyclic hydrocarbon radicals having from 3 to 6 carbon atoms, such as, cyclopropyl, cyclobutyl, cyclopentyl and cyclohexyl; and the term "halo" is generic to halogens of atomic weight less than 127, i.e. fluoro, chloro, bromo and iodo.

The compounds of formula (I) wherein L, Ar, $Ar^1$ and X are as above-defined provided that when Ar and $Ar^1$ are each phenyl or substituted phenyl and X is hydrogen, then said L is other than cycloalkyl having from 5 to 6 carbon atoms, as well as their pharmaceutically acceptable acid addition salts, are deemed to be novel and as useful therapeutic agents herein they constitute an important feature of this invention.

The subject compounds of formula (I) wherein Ar, $Ar^1$ and X are as previously defined and L is hydrogen, (I-a), may generally be prepared starting from a piperidine derivative of formula (II), wherein Ar and X are as previously defined and P is an appropriate protecting group such as, for example, phenylmethyl, lower alkyloxycarbonyl or phenylmethoxycarbonyl, by first acylating (II) with an appropriate arylacetyl halide of formula (III), preferably the chloride, and thereafter eliminating the protecting group P of the thus obtained (IV) following art-known procedures.

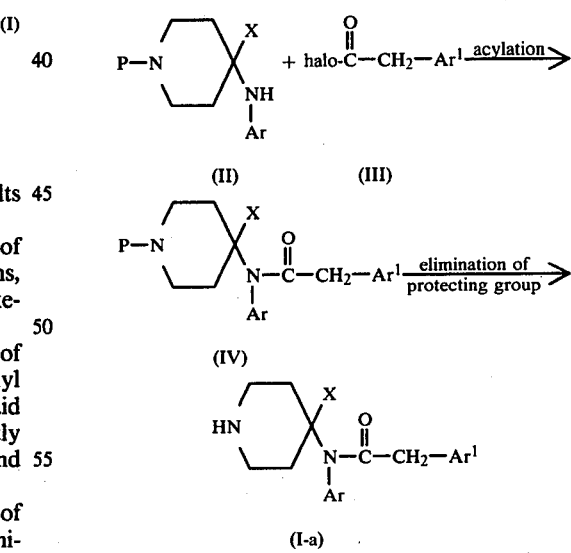

The acylation of (II) with (III) may be carried out following art-known N-acylating procedures, e.g. by stirring and refluxing the reactants together in a suitable reaction-inert organic solvent, preferably in the presence of an appropriate base. Suitable solvents which may be employed include, for example, aromatic hydrocarbons such as, for example, benzene, methylbenzene and dimethylbenzene, and halogenated hydrocarbons such as trichloromethane. Appropriate bases include, for example, alkali metal carbonates and hydrogen carbonates, alkali metal amides such as sodium amide, and organic bases such as, for example, pyridine and N,N-diethylethanamine.

The elimination of the protecting group P may be performed according to generally known methodologies. When the protecting group is phenylmethyl or phenylmethoxycarbonyl it is easily removed by catalytic hydrogenation using an appropriate catalyst, e.g., palladium-on-charcoal, and when the protecting group is lower alkyloxycarbonyl its elimination may easily be accomplished by acid or alkaline hydrolysis. Acid hydrolysis may be carried out using a strong mineral acid, e.g., hydrochloric, hydrobromic or sulfuric acid and alkaline hydrolysis is conveniently carried out using alcoholic alkali, e.g. potassium hydroxide in 2-propanol.

The compounds of formula (I) wherein Ar, $Ar^1$ and X are as previously defined, and L is as previously defined but other than hydrogen, said L being represented by $L^1$ and said compounds by the formula (I-b), may be prepared by introducing the appropriate $L^1$-substituent into an appropriate compound (I-a), according to known N-alkylating procedures.

Conveniently said N-alkylation may be achieved by reacting (I-a) with an appropriate reactive ester of the formula $L^1$-Y, (V), wherein $L^1$ is as defined hereinabove and Y is an appropriate reactive ester radical such as, for example, halo, or a sulfonyl radical such as methanesulfonyl or 4-methylbenzenesulfonyl. The foregoing reaction may be carried out in the usual manner, for example, by stirring and refluxing the reactants together in an appropriate reaction-inert organic solvent such as, for example, a lower alkanol, e.g., methanol, ethanol, propanol, butanol and the like alcohols; an aromatic hydrocarbon, e.g. benzene, methylbenzene, dimethylbenzene, and the like; a ketone, e.g., 4-methyl-2-pentanone; an ether, e.g., 1,4-dioxane, 1,1'-oxybisethane and the like; N,N-dimethylformamide; nitrobenzene; and the like. In order to bind the acid which is liberated during the course of the reaction there may be added an appropriate base such as, for example, sodium or potassium carbonate or hydrogen carbonate or an organic base such as, for example, N,N-diethylethanamine. A small amount of an alkali metal iodide, e.g., potassium iodide, may be added to enhance the reaction rate, especially when the reactive ester (V) is a chloride or bromide.

When $L^1$ in the compounds (I-b) has the meaning of alkyl, cycloalkyl or cycloalkyl-lower alkyl and when the carbon atom attached to the piperidine nitrogen has thereon at least one hydrogen atom, the introduction of said $L^1$ may equally well be performed by catalytic hydrogenation of a mixture of an appropriate aldehyde or ketone corresponding to the alcohol $L^1$-OH, and a compound of formula (I-a) in the presence of an appropriate catalyst such as, for example, palladium-on-charcoal. In order to improve the selectivity of the hydrogenation reaction there may be added to the mixture a small amount of an appropriate catalyst poison such as, for example, thiophene.

Alternatively the compounds (I-b) may be obtained by the reaction of $L^1Y$ with a phenylmethyl-substituted compound of formula (II-1) to form a quaternary piperidinium salt of formula (VI), and subsequent reductive elimination of the phenylmethyl group. The quaternization reaction may be carried out, for example, by heating the reactants together in an appropriate solvent, such as acetonitrile, and elimination of the phenylmethyl group may be performed by catalytic hydrogenation using palladium-on-charcoal catalyst. The foregoing reactions are illustrated in the following schematic representation.

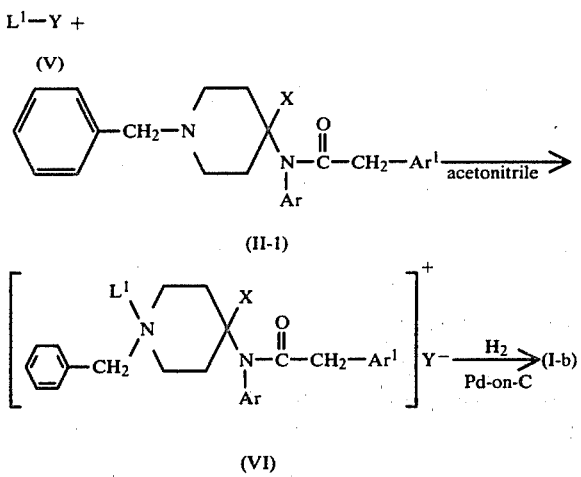

Still another method of preparing the compounds of formula (I-b) consists in acylating an appropriate N-aryl-1-$L^1$-4-piperidinamine of formula (VII) with an appropriate arylacetyl halide of formula (III) according to well-known N-acylating procedures as described hereinabove for the preparation of (IV) starting from (II) and (III).

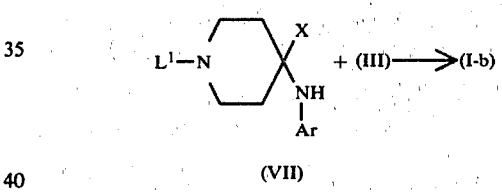

When $Ar^1$ in the compounds (I-b) has the meaning of a substituted phenyl group having as substituents one or two hydroxylgroups, alone or together with other substituents, it is appropriate to protect said hydroxylgroups in the corresponding starting materials (III) with an appropriate protecting group such as lower alkyloxycarbonyl, whereupon a corresponding derivative of (I-b) is obtained, the protecting group of which is easily removed by alkaline hydrolysis using for example diluted aqueous alkali.

The subject compound may be converted to the pharmaceutically acceptable acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form.

The intermediates used as starting materials in the foregoing preparations, a number of which are known compounds, may be prepared as follows.

The intermediates of formula (II) wherein X stands for hydrogen, (II-a), are conveniently obtained as follows. A 4-piperidinone of formula (VIII), having in the 1-position an appropriate protecting group P, is subjected to a condensation reaction with an appropriate arylamine (IX), e.g. by stirring and refluxing the reactants under azeotropic water removal in an appropriate organic solvent, preferably an aromatic hydrocarbon such as benzene, methylbenzene or dimethylbenzene in the presence of an appropriate acid such as, for example, 4-methylbenzenesulfonic acid, acetic acid, hydrochloric acid and the like. The resulting Schiff base (X) is then reduced with an appropriate reducing agent such as, for example, sodium borohydride, or by catalytic hydrogenation using, for example, platinum oxide catalyst, to obtain the corresponding N-aryl-4-piperidineamine (II-a).

The foregoing reactions are more clearly illustrated in the following schematic representation:

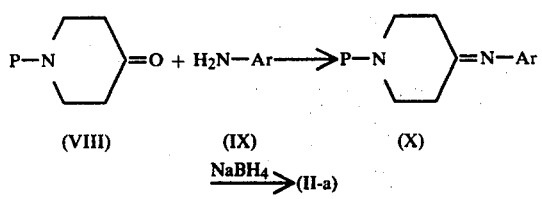

Intermediates of formula (VII) wherein X is hydrogen, (VII-a), are conveniently prepared starting from (II-a) by first eliminating the protecting group P in the usual manner to obtain a N-aryl-4-piperidinamine of formula (XI) and thereafter introducing the $L^1$-substituent as described hereinbefore for the preparation of (I-b) starting from (I-a).

When $L^1$ in the intermediates (VII-a) has the meaning of a methyl group, (VII-a-1), they may directly be obtained by the reduction of an intermediate (II-a) wherein P is a lower alkyloxycarbonyl group, (II-a-2), with an appropriate reducing agent such as, for example lithium aluminium hydride. The foregoing reactions are illustrated in the following schematic representation:

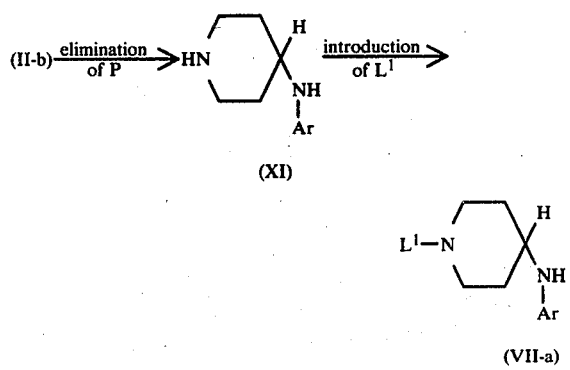

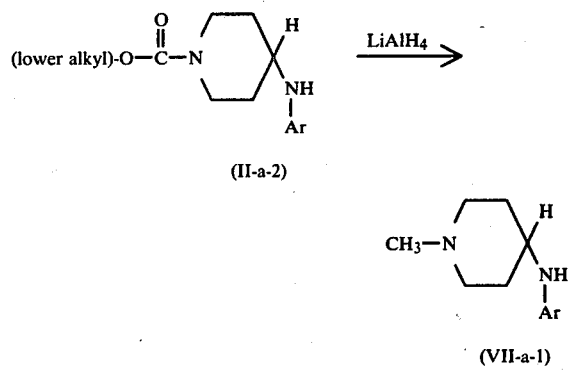

Intermediates of formula (II) wherein X stands for lower alkyloxycarbonyl, (II-b), may be prepared as follows.

1-Phenylmethyl-4-piperidinone (XII) is reacted with an appropriate arylamine (IX) and an alkali metal cyanide, for example potassium cyanide, in an aqueous organic carboxylic acid system, such as acetic acid, or in an aqueous lower alkanol in the presence of an equivalent of an inorganic acid, such as hydrochloric acid, whereby introduction of the nitrile function and of the amine function is effected in the 4-position of the piperidine nucleus, yielding an intermediate of formula (XIII).

The nitrile (XIII) is then converted into the amide (XIV) by acid hydrolysis. Advantageously one may use a concentrated strong, aqueous, inorganic acid for this purpose, such as hydrochloric acid, phosphoric acid and, preferably, sulfuric acid. The amide (XIV) is then further hydrolyzed to obtain the corresponding carboxylic acid (XV), by the application of known amide-to-acid hydrolysis procedures, for example by treating (XIV) with a diluted strong acid, e.g., hydrochloric or sulfuric acid, or by alkaline hydrolysis using an appropriate base, e.g. sodium or potassium hydroxide. The thus obtained carboxylic acid (XV) is in turn converted into a metal salt thereof, preferably the sodium salt (XVI), by the reaction with alkali, e.g., with sodium hydroxide. The carboxylic acid (XV) need not necessarily be isolated or purified, but may be utilized as a crude mixture in the preparation of (XVI), or the salt may be obtained directly when alkaline hydrolysis is carried out.

The salt (XVI) is then converted into the desired ester (II-b) wherein P stands for phenylmethyl (II-b-1) by the reaction with an appropriate halo-lower alkane (XVII) in an appropriate solvent such as, for example, hexamethylphosphoric triamide.

Alternatively the esters (II-b-1) may be prepared by converting the acid (XV) into an acyl halide (XVIII) in the usual manner, by the treatment with an appropriate halogenating agent, e.g. with sulfinyl chloride, and reacting said acyl halide with an appropriate lower alkanol or simply by reacting the acid with an appropriate alcohol in the presence of an acid.

The foregoing reactions are more clearly illustrated in the following schematic representation:

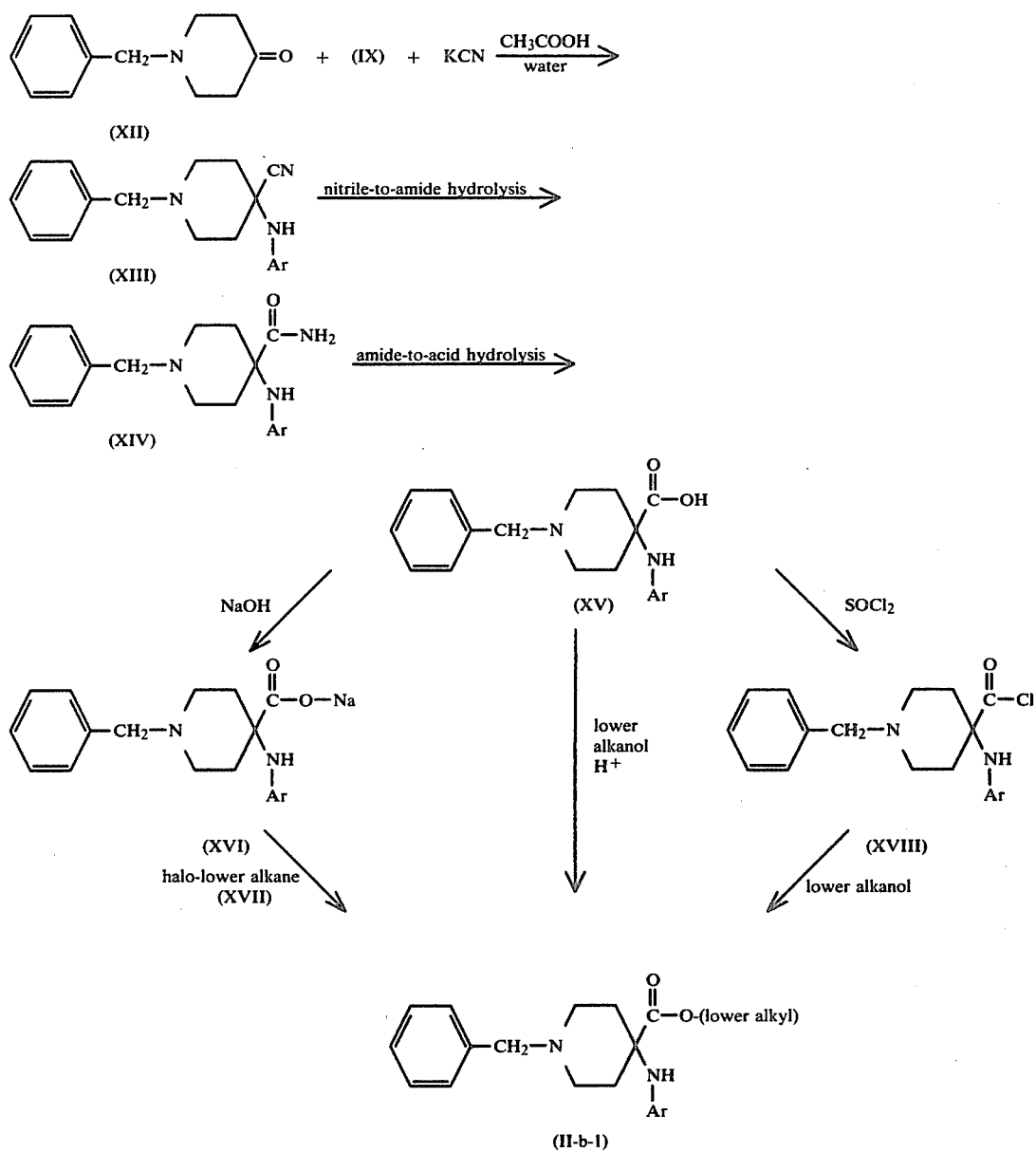

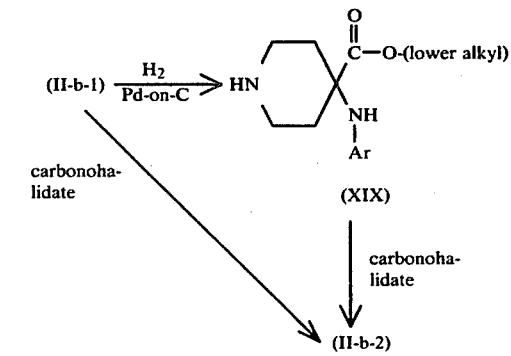

The intermediates of formula (II-b) wherein P stands for lower alkyloxycarbonyl or phenylmethoxycarbonyl (II-b-2) are easily derived from (II-b-1) by eliminating the protecting phenylmethyl group and thereafter introducing into the thus obtained (XIX) the lower alkyloxycarbonyl or phenylmethoxycarbonyl group according to art-known procedures, e.g., by the reaction of (XIX) with an appropriate lower alkyl or phenylmethyl carbonohalidate, or directly by the reaction of (II-b-1) with a lower alkyl or phenylmethyl carbonohalidate whereupon the phenylmethyl group of (II-b-1) is replaced by the desired lower alkyloxycarbonyl or phenylmethoxycarbonyl group.

Intermediates of formula (VII) wherein X stands for lower alkyloxycarbonyl (VII-b) are conveniently prepared by introducing the $L^1$-group into an intermediate (XIX) according to the procedures described hereinbefore.

The intermediates of formulas (II) and (VII) wherein X stands for lower alkyloxymethyl, (II-c) and (VII-c) respectively, may be prepared as follows.

An appropriate lower alkyl ester of formula (II-b) is reduced with an appropriate reducing agent such as, for example, sodium dihydro-bis(2-methoxyethoxy)aluminate (Red-Al) in an appropriate organic solvent such as, for example, benzene, or with lithium borohydride to obtain a 4-piperidinemethanol of formula (XX). Said (XX) is then subjected to an O-alkylation reaction with an appropriate alkylating agent. The O-alkylation step may be carried out by the reaction of (XX) with an appropriate halo-lower alkane or di(lower alkyl) sulfate in an appropriate organic solvent such as, for example, benzene, methylbenzene, dimethylbenzene, tetrahydrofuran and the like, in the presence of an appropriate quaternary ammonium salt such as N,N,N-triethylbenzenemethanaminium chloride, yielding the desired intermediate (II-c). The intermediates (VII-c) can be prepared by first eliminating the protecting group of (II-c) and thereafter introducing $L^1$-substituent into the thus obtained intermediate (XXI) according to the procedures described hereinbefore.

Otherwise the intermediates (VII-c) may still be prepared by reducing an appropriate alkyl ester of formula (VII-b) to the corresponding 4-piperidinemethanol (XXII) in a similar manner as described hereinabove for the preparation of (XX) starting from (II-b), and thereafter subjecting (XXII) to an O-alkylation reaction with an appropriate lower alkyl alkylating agent according to the procedures indicated for the preparation of (II-c) starting from (XX).

The foregoing procedures are illustrated hereafter.

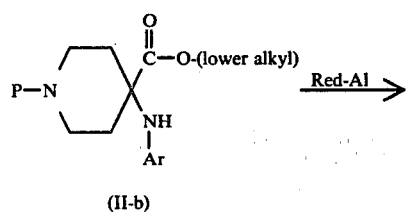

(II-b)

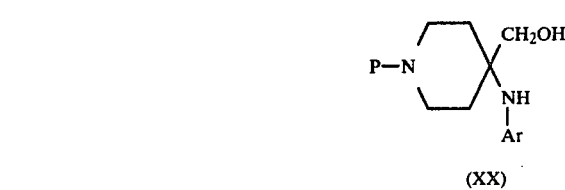

(XX)

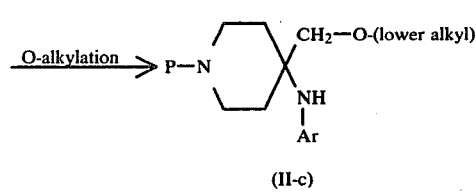

(II-c)

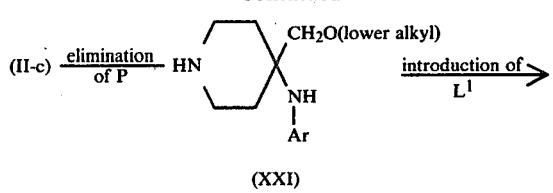

(XXI)

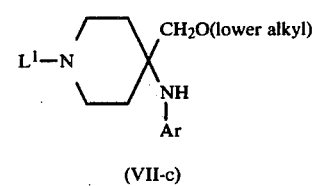

(VII-c)

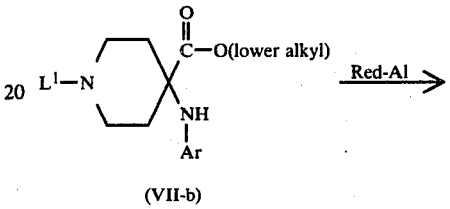

(VII-b)

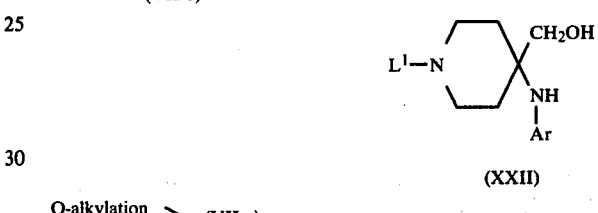

(XXII)

 (VII-c)

The compounds of formula (I) and their pharmaceutically acceptable acid addition salts show excellent antiarrhythmic properties and as such they are useful in the normalization of irregular cardial rhythms. The antiarrhythmic effect of the compounds of this invention is clearly illustrated in the following experiment in dogs. The test is carried out under neuroleptanalgesia (1 ml per 10 kg bodyweight of fentanyl (0.4 mg/ml) and droperidol (20 mg/ml)). About 16 hours after the ligation of the anterior descendent branch of the left coronary artery, dogs exhibit a multifocal ventricular arrhythmia.

The test compounds were given intraveneously after a control period of 30 minutes, and the following criteria were adopted:
 0 :no effect
 + :decrease of the number of premature beats and increase of the number of normal beats by at least 30% as compared to the control value.
 + + :decrease of the number of premature beats and increase of the number of normal beats by at least 50% as compared to the control value.
 + + + :normalisation of cardial rhythm or decrease of the number of premature beats and increase of the number of normal beats by at least 75% as compared to the control value.

The results obtained in this experiment are given in the following tables. The compounds listed therein are not given for the purpose of limiting the invention thereto but only to exemplify the useful antiarrhythmic properties of all the compounds within the scope of formula (I).

Table I $$\text{L-N}\underset{}{\bigcirc}\overset{H}{\underset{Ar}{C}}-\overset{O}{\underset{}{N-C}}-CH_2-Ar^1$$

| L | Ar | Ar$^1$ | base or salt form | Antiarrhythmic effect in dogs 2.5 mg/kg | 5 mg/kg |
|---|---|---|---|---|---|
| —CH$_3$ | 4-Cl—C$_6$H$_4$ | C$_6$H$_5$ | base | ++ | — |
| —C$_2$H$_5$ | 4-Cl—C$_6$H$_4$ | C$_6$H$_5$ | HCl | ++ | +++ |
| -nC$_3$H$_7$ | 4-Cl—C$_6$H$_4$ | C$_6$H$_5$ | HCl | — | +++ |
| -iC$_3$H$_7$ | 4-Cl—C$_6$H$_4$ | C$_6$H$_5$ | HCl | ++ | +++ |
| -nC$_4$H$_9$ | 4-Cl—C$_6$H$_4$ | C$_6$H$_5$ | HCl | ++ | ++ |
| —CH(CH$_3$)—CH$_2$—CH$_3$ | 4-Cl—C$_6$H$_4$ | C$_6$H$_5$ | HCl | 0 | ++ |
| -nC$_6$H$_{13}$ | 4-Cl—C$_6$H$_4$ | C$_6$H$_5$ | HCl | 0 | +++ |
| —CH$_2$-cyclopropyl | 4-Cl—C$_6$H$_4$ | C$_6$H$_5$ | HCl | ++ | +++ |
| cyclopentyl | 4-Cl—C$_6$H$_4$ | C$_6$H$_5$ | base | + | ++ |
| -iC$_3$H$_7$ | 4-F—C$_6$H$_4$ | C$_6$H$_5$ | base | + | ++ |
| -iC$_3$H$_7$ | 2-Cl—C$_6$H$_4$ | C$_6$H$_5$ | base | ++ | — |
| -iC$_3$H$_7$ | 3-Cl—C$_6$H$_4$ | C$_6$H$_5$ | HCl | + | ++ |
| -iC$_3$H$_7$ | 4-Cl—C$_6$H$_4$ | 4-F—C$_6$H$_4$ | HCl | ++ | ++ |
| -iC$_3$H$_7$ | 4-Cl—C$_6$H$_4$ | 2-Cl—C$_6$H$_4$ | base | + | +++ |
| -iC$_3$H$_7$ | 4-Cl—C$_6$H$_4$ | 3-Cl—C$_6$H$_4$ | base | ++ | +++ |
| -iC$_3$H$_7$ | 4-Cl—C$_6$H$_4$ | 4-Cl—C$_6$H$_4$ | base | + | ++ |
| -iC$_3$H$_7$ | 4-Cl—C$_6$H$_4$ | 3,4-(Cl)$_2$—C$_6$H$_3$ | base | ++ | +++ |
| -iC$_3$H$_7$ | 4-Cl—C$_6$H$_4$ | 4-Br—C$_6$H$_4$ | base | + | ++ |
| -iC$_3$H$_7$ | 4-Cl—C$_6$H$_4$ | 3-CH$_3$—C$_6$H$_4$ | HCl | + | ++ |
| -iC$_3$H$_7$ | 4-Cl—C$_6$H$_4$ | 4-CH$_3$—C$_6$H$_4$ | HCl | ++ | ++ |
| -iC$_3$H$_7$ | 4-Cl—C$_6$H$_4$ | 3-OCH$_3$—C$_6$H$_4$ | base | ++ | +++ |
| -iC$_3$H$_7$ | 2,6-(Cl)$_2$—C$_6$H$_3$ | 4-Cl—C$_6$H$_4$ | base | ++ | |
| -iC$_3$H$_7$ | 3,4-(Cl)$_2$—C$_6$H$_3$ | C$_6$H$_5$ | HCl | + | +++ |
| -iC$_3$H$_7$ | 3,4-(Cl)$_2$—C$_6$H$_3$ | 4-Cl—C$_6$H$_4$ | HCl | + | ++ |
| -iC$_3$H$_7$ | 4-Br—C$_6$H$_4$ | C$_6$H$_5$ | base | ++ | ++ |
| -iC$_3$H$_7$ | 2,6-(CH$_3$)$_2$—C$_6$H$_3$ | C$_6$H$_5$ | HCl | ++ | ++ |
| -iC$_3$H$_7$ | 2-Cl,6-CH$_3$—C$_6$H$_3$ | C$_6$H$_5$ | HCl | ++ | — |
| -iC$_3$H$_7$ | 2,6-(CH$_3$)$_2$—C$_6$H$_3$ | 4-Cl—C$_6$H$_4$ | HCl | ++ | +++ |
| cyclopentyl | 4-Cl—C$_6$H$_4$ | 4-F—C$_6$H$_4$ | base | ++ | ++ |
| cyclopentyl | 4-Cl—C$_6$H$_4$ | 2-Cl—C$_6$H$_4$ | base | + | ++ |
| cyclopentyl | 4-Cl—C$_6$H$_4$ | 3-CH$_3$—C$_6$H$_4$ | base | + | +++ |
| cyclopentyl | 4-Cl—C$_6$H$_4$ | 4-CH$_3$—C$_6$H$_4$ | HCl | ++ | ++ |
| cyclopentyl | 4-Cl—C$_6$H$_4$ | 3-OCH$_3$—C$_6$H$_4$ | base | ++ | — |
| —C$_2$H$_5$ | 4-Cl—C$_6$H$_4$ | 4-F—C$_6$H$_4$ | base | + | +++ |
| —C$_2$H$_5$ | 4-Cl—C$_6$H$_4$ | 3-CH$_3$—C$_6$H$_4$ | base | ++ | +++ |
| —C$_2$H$_5$ | 4-Cl—C$_6$H$_4$ | 4-CH$_3$—C$_6$H$_4$ | base | + | ++ |
| —C$_2$H$_5$ | 4-Cl—C$_6$H$_4$ | 3-OCH$_3$—C$_6$H$_4$ | base | + | +++ |
| —C$_2$H$_5$ | 2,6-(CH$_3$)$_2$—C$_6$H$_3$ | C$_6$H$_5$ | base | ++ | ++ |
| -nC$_3$H$_7$ | 2,6-(CH$_3$)$_2$—C$_6$H$_3$ | C$_6$H$_5$ | (COOH)$_2$ | ++ | +++ |
| -iC$_3$H$_7$ | C$_6$H$_5$ | 3-CH$_3$—C$_6$H$_4$ | HCl | +++ | — |

Table I-continued $$\text{L-N}\overset{\phantom{x}}{\underset{\displaystyle\diagup}{\bigcirc}}\overset{H}{\underset{\text{Ar}}{N}}-\overset{O}{\underset{\phantom{x}}{C}}-CH_2-Ar^1$$

| L | Ar | Ar¹ | base or salt form | Antiarrhythmic effect in dogs 2.5 mg/kg | 5 mg/kg |
|---|---|---|---|---|---|
| cyclopentyl | $C_6H_5$ | $C_6H_5$ | base | ++ | +++ |
| cyclopentyl | $C_6H_5$ | 3-Cl—$C_6H_4$ | base | +++ | — |
| cyclopentyl | $C_6H_5$ | 4-Cl—$C_6H_4$ | base | + | +++ |
| cyclohexyl (H) | $C_6H_5$ | 3-Cl—$C_6H_4$ | HCl | ++ | +++ |
| —$C_2H_5$ | 4-Cl—$C_6H_4$ | 2-thienyl | HCl | 0 | ++ |
| -n$C_3H_7$ | 4-Cl—$C_6H_4$ | 2-thienyl | HCl | + | ++ |
| —$CH_2$—CH=$CH_2$ | 4-Cl—$C_6H_4$ | 2-thienyl | HCl | 0 | ++ |
| -n$C_3H_7$ | 2,6-($CH_3$)$_2$—$C_6H_3$ | 2-thienyl | (COOH)$_2$ | ++ | ++ |
| -$C_3H_7$ | $C_6H_5$ | 2-thienyl | (COOH)$_2$ | + | +++ |
| cyclopentyl | $C_6H_5$ | 2-thienyl | base | +++ | — |
| -i$C_3H_7$ | 4-Cl—$C_6H_4$ | 2-thienyl | HCl | ++ | +++ |
| -i$C_3H_7$ | 2,6-($CH_3$)$_2$—$C_6H_3$ | 2-thienyl | HCl | ++ | ++ |
| -i$C_3H_7$ | 2-pyridyl | $C_6H_5$ | base | ++ | ++ |
| -i$C_3H_7$ | 2-pyridyl | 3-Cl—$C_6H_4$ | base | +++ | — |
| -i$C_3H_7$ | 2-pyridyl | 4-Cl—$C_6H_4$ | base | ++ | +++ |

Table I-continued

[Structure: L—N(piperidine ring)—C(H)(NHCOCH₂—Ar¹)(N—Ar)]

| L | Ar | Ar¹ | base or salt form | Antiarrhythmic effect in dogs 2.5 mg/kg | 5 mg/kg |
|---|---|---|---|---|---|
| -C₃H₇ | 2-pyridyl | 3-CH₃—C₆H₄ | (COOH)₂ | + | ++ |
| cyclopentyl | 2-pyridyl | C₆H₅ | base | + | ++ |
| cyclopentyl | 2-pyridyl | 4-Cl—C₆H₄ | base | ++ | +++ |
| cyclopentyl | 2-pyridyl | 3-CH₃—C₆H₄ | base | ++ | ++ |
| -iC₃H₇ | 3-pyridyl | C₆H₅ | base | ++ | ++ |
| -iC₃H₇ | 3-pyridyl | 3-Cl—C₆H₄ | base | ++ | ++ |
| -iC₃H₇ | 3-pyridyl | 4-Cl—C₆H₄ | base | + | ++ |
| -iC₃H₇ | 3-pyridyl | 3-CH₃—C₆H₄ | base | + | ++ |
| cyclopentyl | 3-pyridyl | 3-Cl—C₆H₄ | 2 HCl . ½ H₂O | ++ | +++ |
| cyclopentyl | 3-pyridyl | 4-Cl—C₆H₄ | base | + | ++ |
| cyclopentyl | 3-pyridyl | 3-CH₃—C₆H₄ | HOOCCH=CHCOOH | ++ | +++ |
| H | 4-Cl—C₆H₄ | C₆H₅ | HCl | − | ++ |
| H | 2-Cl—C₆H₄ | C₆H₅ | base | + | ++ |
| H | 4-Cl—C₆H₄ | 4-F—C₆H₄ | base | + | ++ |
| H | 4-Cl—C₆H₄ | 3-(OCH₃)—C₆H₄ | base | + | ++(+) |

Table I-continued

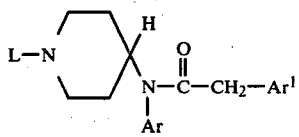

| L | Ar | Ar¹ | base or salt form | Antiarrhythmic effect in dogs | |
|---|---|---|---|---|---|
| | | | | 2.5 mg/kg | 5 mg/kg |
| H | 4-Cl—C$_6$H$_4$ | 2-Cl—C$_6$H$_4$ | base | + | ++(+) |

TABLE II

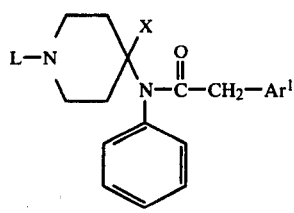

| L | X | Ar¹ | Base or Salt form | Antiarrhythmic effect in dogs | |
|---|---|---|---|---|---|
| | | | | 2.5 mg/kg | 5 mg/kg |
| cyclopentyl | COOOCH$_3$ | 3-Cl—C$_6$H$_4$ | base | + | ++ |
| cyclopentyl | COOC$_2$H$_5$ | 3-Cl—C$_6$H$_4$ | HOOC—CH=CH—COOH | + | ++ |
| cyclopentyl | COOC$_2$H$_5$ | 4-Cl—C$_6$H$_4$ | HOOC—CH=CH—COOH | 0 | ++ |
| cyclopentyl | COOC$_2$H$_5$ | 3-CH$_3$—C$_6$H$_4$ | HOOC—CH=CH—COOH | ++ | +++ |
| iC$_3$H$_7$ | CH$_2$—OCH$_3$ | C$_6$H$_5$ | HCl | ++ | ++(+) |

As a result of the useful anti-arrhythmic properties of the compounds of formula I and the pharmaceutically acceptable acid addition salts thereof, there is also provided by this invention a method of treating cardiac arrhythmia which comprises the systemic administration to warm-blooded animals of an effective anti-arrhythmic amount of at least one compound of the formula (I) or pharmaceutically acceptable acid addition salt thereof. Although the amount of the anti-arrhythmic compound to be administered may vary within rather wide limits, depending on the particular circumstances of the case, doses of from about 50 mg to about 500 mg, when administered from 1 to 4 times a day to adult humans, are generally found effective.

It has been found that certain of the compounds of formula I are surprisingly active upon oral administration, which is a highly desirable property in view of their ease of administration. Such compounds are those wherein X, Ar and Ar¹ are as previously defined and L is an alkyl radical. In view of their potent anti-arrhythmic properties and their excellent oral activity, the latter compounds constitute a preferred genus within the scope of formula (I). Especially preferred compounds are those wherein L is a lower alkyl radical having from 1 to 4 carbon atoms, and in particular 1-methyl-ethyl.

In view of their useful anti-arrhythmic activity, the subject compounds may be formulated into various pharmaceutical forms for administration purposes. To prepare the pharmaceutical compositions of this invention, an effective anti-arrhythmic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention. Unless otherwise stated all parts therein are by weight.

EXAMPLE 1

A mixture of 19 parts of 1-(phenylmethyl)-4-piperidinone, 11.8 parts of 3-pyridinamine, 120 parts of methylbenzene and a small volume of 4-methylbenzenesulfonic acid is stirred and refluxed for 5 hours. (The reaction vessel is provided with reflux-condensor and water-separator). After the calculated amount of water is separated, the solvent is evaporated. The oily residue is dissolved in 800 parts of 2,2'-oxybispropane and evaporated again, yielding 27 parts of N-[1-(phenylmethyl)-4-piperidinylidene]-3-pyridinamine as a yellow-brown oil.

To a stirred solution of 27 parts of N-[1-(phenylmethyl)-4- piperidinylidene]-3-pyridinamine in 40 parts of ethanol are added portionwise 3.8 parts of sodium borohydride. After the addition is complete, the whole is heated to 50° C. The solvent is evaporated. The oily residue is dissolved in 150 parts of hydrochloric acid 1 N and filtered. The filtrate is rendered alkaline with ammonium hydroxide and extracted with methylbenzene. The organic layer is dried over magnesium sulfate, filtered and evaporated. The solid residue is washed with 2,2'-oxybispropane and dried, yielding 14 parts of N-[1-(phenylmethyl)-4-piperidinyl]-3-pyridinamine; mp. 131°-133° C.; beige, amorphous powder.

A mixture of 20 parts of N-[1-(phenylmethyl)-4-piperidinyl]-3-pyridinamine, 160 parts of methanol, 30 parts of water and 12 parts of a concentrated hydrochloric acid solution is hydrogenated at normal pressure and at a temperature between 22°-39° C., in the presence of 7 parts of palladium-on-charcoal catalyst 10%. After the calculated amount of hydrogen is taken up, hydrogenation is stopped. The catalyst is filtered off and the filtrate is evaporated. The oily residue is dissolved in water. This solution is rendered alkaline with ammonium hydroxide, saturated with solid potassium carbonate and then extracted with methylbenzene. The extract is dried over potassium carbonate and evaporated. The solid residue is recrystallized from a mixture of 40 parts of benzene and 32 parts of 1,1'-oxybisethane, yielding 3 parts of N-(4-piperidinyl)-3-pyridinamine; mp. 127°-129° C.

EXAMPLE II

A mixture of 171.2 parts of ethyl 4-oxo-1-piperidinecarboxylate, 159.5 parts of 4-chlorobenzenamine, 1520 parts of anhydrous methylbenzene and a few crystals of 4-methylbenzenesulfonic acid is stirred and refluxed for 7 hours. (The reaction vessel is provided with a reflux-condensor and water-separator). The methylbenzene is evaporated and the oily residue is distilled in vacuo, yielding 192 parts of oily ethyl 4-[(4-chlorophenyl)imino]-1-piperidinecarboxylate; bp. 171°-176° C. at 0.4 mm. pressure.

EXAMPLE III

By repeating the procedure of Example II and using an equivalent amount of an appropriate arylamine in place of the 4-chlorobenzenamine used therein, the following compounds are obtained:

$$CH_3-CH_2-O-\overset{O}{\underset{\|}{C}}-N\diagup\hspace{-1em}\diagdown=N-Ar$$

| Ar | bp. at indicated pressure |
|---|---|
| 2-Cl—C$_6$H$_4$ | 160°-165° C./0.5-0.6 mm. |
| 2,6-(CH$_3$)$_2$—C$_6$H$_3$ | 142°-145° C./0.01 mm. |
| 2-Cl, 6-CH$_3$—C$_6$H$_3$ | 195°-200° C./0.2 mm. |
| 4-F—C$_6$H$_4$ | 145°-147° C./0.01 mm. |
| 3,4-(Cl)$_2$—C$_6$H$_3$ | 190°-200° C./0.02-0.03 mm. |
| 3-Cl—C$_6$H$_4$ | 165°-170° C./0.01-0.02 mm. |
| 4-Br—C$_6$H$_4$ | 180°-183° C./0.1 mm. |
| 2,5-(Cl)$_2$—C$_6$H$_3$ | — |
| 2-pyridinyl | — |

EXAMPLE IV

A mixture of 171 parts of ethyl 4-oxo-1-piperidinecarboxylate, 162 parts of 2,6-dichlorobenzenamine, 800 parts of dimethylbenzene and 1 part of 4-methylbenzenesulfonic acid is stirred and refluxed with water-separator. The reaction mixture is evaporated, yielding 250 parts of ethyl 4-[(2,6-dichlorophenyl)imino]-1-piperidinecarboxylate as a residue.

EXAMPLE V

A mixture of 34 parts of ethyl 4-oxo-1-piperidinecarboxylate, 20 parts of 2-pyrimidinamine, 8 drops of acetic acid and 90 parts of methylbenzene is stirred and refluxed for 28 hours with water-separator. The reaction mixture is evaporated, yielding 50 parts of ethyl 4-(2-pyrimidinylimino)-1-piperidinecarboxylate as a residue.

EXAMPLE VI

To a warm solution of 192 parts of ethyl 4-[(4-chlorophenyl)imino]-1-piperidinecarboxylate in 560 parts of methanol is added portionwise 23.5 parts of sodium borohydride at 50° C. and over a period of one hour. After the addition is complete, the mixture is stirred at the same temperature for 2 hours. The methanol is evaporated. The solid residue is heated with ±600 parts of water and the product is extracted with benzene. The extract is dried over magnesium sulfate and evaporated. The oily residue solidifies on treating with 2,2'-oxybispropane. The solid is filtered off and dried, yielding 122 parts of ethyl 4-[(4-chlorophenyl)amino]-1-piperidinecarboxylate; mp. 115°–118° C.

EXAMPLE VII

Following the procedure of Example VI and using an equivalent amount of an appropriate ethyl 4-arylimino-1-piperidinecarboxylate, the following compounds are prepared:

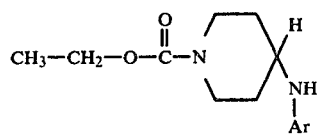

| Ar | mp./bp. |
|---|---|
| 2-Cl—C6H4 | mp. 89°–93° C. |
| 2-Cl, 6-CH3—C6H3 | mp. 99.5° C. |
| 4-F—C6H4 | bp. 140°–142° C./0.01 mm. |
| 3,4-(Cl)2—C6H3 | mp. 113.5° C. |
| 3-Cl—C6H4 | mp. 72° C. |
| 4-Br—C6H4 | mp. 116.5° C. |
| 2,5-(Cl)2—C6H3 | mp. 107.2°–110.3° C. |
| 2-pyrimidinyl | — |

EXAMPLE VIII

To a stirred and refluxing mixture of 250 parts of ethyl 4-[(2,6-dichlorophenyl)imino]-1-piperidinecarboxylate in 160 parts of methanol and 160 parts of 2-propanol are added portionwise 30 parts of sodium borohydride. Upon completion, stirring at reflux temperature is continued for one hour. The warm reaction mixture is poured onto water and the product is extracted with methylbenzene. The extract is dried and evaporated. The residue is crystallized from a mixture of 160 parts of 2,2'-oxybispropane and 160 parts of petroleumether, yielding 96 parts of ethyl 4-[(2,6-dichlorophenyl)amino]-1-piperidinecarboxylate; mp. 107.2°–116.6° C.

EXAMPLE IX

A mixture of 45 parts of ethyl 4-[(2,6-dimethylphenyl)imino]-1-piperidinecarboxylate, 0.3 parts of platinum dioxide in 160 parts of methanol is hydrogenated at normal pressure and at a temperature between 24° and 35° C. After the calculated amount of hydrogen is taken up, hydrogenation is stopped. The catalyst is filtered off and the filtrate is evaporated. The oily residue is distilled, to yield 30 parts of the oily free base of ethyl 4-[(2,6-dimethylphenyl)amino]-1-piperidinecarboxylate; bp. 148°–153° C. at 0.01 mm. pressure. From this distillate, the hydrochloride salt is prepared in the usual manner in 1,1'-oxybisethane. The precipitated solid salt is filtered off and dried, yielding 28.5 parts of ethyl 4-[(2,6-dimethylphenyl)amino]-1-piperidinecarboxylate hydrochloride; mp. 195.5° C.

A mixture of 10 parts of ethyl 4-[(2,6-dimethylphenyl)amino]-1-piperidinecarboxylate and 135 parts of hydrobromic acid solution 48% is stirred at a temperature between 80° and 110° C. until the evolution of gaseous carbon dioxide is ceased (about one hour). The red-coloured reaction mixture is evaporated in vacuo. The residue is taken up in 56 parts of methylbenzene and the latter is evaporated again. Then evaporation is repeated in a mixture of 24 parts of 2-propanone and 40 parts of methylbenzene. The resulting semi-solid residue is triturated in 80 parts of hot 2-propanone and on cooling, the solid product is precipitated. It is filtered off, washed successively with small amounts of absolute ethanol and 2-propanone and dried, yielding 13 parts of N-(2,6-dimethylphenyl)-4-piperidinamine dihydrobromide; mp. +300° C.

EXAMPLE X

To a stirred and cooled (ice-bath) mixture of 165 parts of ethyl 4-(2-pyridinylimino)-1-piperidinecarboxylate and 736 parts of methanol are added portionwise 29.5 parts of sodium borohydride (exothermic reaction). Upon completion, stirring is continued for 1h.30 at room temperature. The reaction mixture is evaporated. The residue is suspended in 460 parts of water and the suspension is acidified with a concentrated hydrochloric acid solution. The whole is alkalized with ammonium hydroxide and the product is extracted with methylbenzene. The extract is dried, filtered and evaporated. The residue is converted into the ethanedioate salt in 2-propanol and 2,2'-oxybispropane. The salt is filtered off, washed with 2,2'-oxybispropane and dried in vacuo, yielding 38 parts of ethyl 4-(2-pyridinylamino)-1-piperidinecarboxylate ethanedioate.

A mixture of 90 parts of ethyl 4-(2-pyridinylamino)-1-piperidinecarboxylate, 90 parts of potassium hydroxide and 720 parts of 2-propanol is stirred and refluxed for 2 days. The reaction mixture is evaporated. 1000 Parts of water are added to the residue and the product is extracted with dichloromethane. The extract is dried, filtered and evaporated. The residue is crystallized from 2,2'-oxybispropane, yielding 13 parts of N-(4-piperidinyl)-2-pyridinamine.

EXAMPLE XI

A mixture of 7 parts of ethyl 4-(2-pyrimidinylamino)-1-piperidinecarboxylate and 120 parts of hydrobromic acid solution 48% is stirred and refluxed for 2 hours. The reaction mixture is evaporated and the residue is taken up in water. The whole is alkalized with a diluted sodium hydroxide solution while cooling in an ice-bath. The product is extracted with dichloromethane. The extract is dried, filtered and evaporated. The solid residue is stirred in 2,2'-oxybispropane. The product is filtered off and converted into the hydrochloride salt in 2-propanol. The salt is filtered off and crystallized from ethanol, yielding 2 parts of N-(4-piperidinyl)-2-pyrimidinamine dihydrochloride hemihydrate; mp. 268.5° C.

EXAMPLE XII

A mixture of 32.5 parts of methyl 4-(phenylamino)-1-(phenylmethyl)-4-piperidinecarboxylate and 200 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The oily residue solidifies on scratching in 2,2'-oxybispropane. The product is filtered off and dried in vacuo, yielding 20 parts (85%) of methyl 4-(phenylamino)-4-piperidinecarboxylate; mp. 139.1° C.

EXAMPLE XIII

To a stirred solution of 58 parts of ethyl 4-[(4-chlorophenyl)amino]-1-piperidinecarboxylate in 240 parts of benzene is added dropwise a solution of 46.2 parts of benzeneacetyl chloride in 80 parts of benzene at a temperature between 40°–70° C. Upon completion, the whole is stirred and refluxed for 6h.15. The reaction mixture is cooled and filtered. The filtrate is washed successively with water, sodium hydrogen carbonate solution and water, then dried and evaporated in vacuo. The residue is crystallized from 1,1'-oxybisethane, yielding 47 parts of ethyl 4-[N-(4-chlorophenyl)-N-(phenylacetyl)amino]-1-piperidinecarboxylate; mp. 108° C.

EXAMPLE XIV

Following the procedure of Example XIII and using equivalent amounts respectively of an appropriate ethyl 4-arylamino-1-piperidinecarboxylate and of an appropriate arylacetyl chloride in place of the ethyl 4-[(4-chlorophenyl)amino]-1-piperidinecarboxylate and benzeneacetyl chloride used therein, the following compounds are prepared:

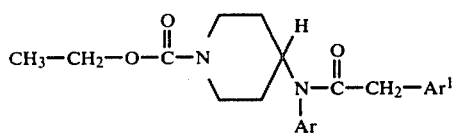

| Ar | Ar¹ | mp. |
|---|---|---|
| 2,6-(CH₃)₂—C₆H₃ | 2-thienyl | 94.5° C. |
| 4-Cl—C₆H₄ | 2-thienyl | 98.5° C. |
| 4-Cl—C₆H₄ | 4-Cl—C₆H₄ | 127.5° C. |
| 4-Cl—C₆H₄ | 4-CH₃—C₆H₄ | 112.5° C. |
| 2-Cl—C₆H₄ | C₆H₅ | 123.0° C. |
| 2-Cl, 6-CH₃—C₆H₃ | C₆H₅ | 114.5° C. |
| 4-F—C₆H₄ | C₆H₅ | 82.0° C. |
| 3,4-(Cl)₂—C₆H₃ | C₆H₅ | 115.0° C. |
| 3-Cl—C₆H₄ | C₆H₅ | 92.0° C. |
| 4-Cl—C₆H₄ | 4-F—C₆H₄ | 109.0° C. |
| 4-Cl—C₆H₄ | 3-CH₃—C₆H₄ | 121.5° C. |
| 4-Br—C₆H₄ | C₆H₅ | 114.5° C. |
| 4-Cl—C₆H₄ | 3-OCH₃—C₆H₄ | 121.2° C. |
| 4-Cl—C₆H₄ | 2-Cl—C₆H₄ | 139.3° C. |
| 4-Cl—C₆H₄ | 3-Cl—C₆H₄ | 142.7° C. |
| 2-Cl, 6-CH₃—C₆H₃ | 4-Cl—C₆H₄ | 95.6° C. |
| 4-Cl—C₆H₄ | 2,6-(CH₃)₂—C₆H₃ | 120.4° C. |
| 3,4-(Cl)₂—C₆H₃ | 4-Cl—C₆H₄ | 136.9° C. |
| 2,5-(Cl)₂—C₆H₃ | 4-Cl—C₆H₄ | 107.0° C. |
| 2,6-(Cl)₂—C₆H₃ | 4-Cl—C₆H₄ | 140.0° C. |

EXAMPLE XV

To a stirred solution of 8 parts of ethyl 4-[(2,6-dimethylphenyl)amino]-1-piperidinecarboxylate in 4 parts of pyridine and 80 parts of benzene are added dropwise 7.7 parts of benzeneacetyl chloride in 40 parts of benzene. After the addition is complete, the whole is heated to reflux and stirred at reflux temperature for 3h.45. The reaction mixture is cooled and filtered. The benzene-phase is washed with water and then with sodium hydrogen carbonate solution and with water. After evaporation, an oily residue is obtained, which solidifies on triturating in 1,1'-oxybisethane, to yield 5 parts of ethyl 4-[N-(2,6-dimethylphenyl)-N-(phenylacetyl)amino]-1-piperidinecarboxylate; mp. 106° C.

EXAMPLE XVI

To a stirred solution of 15 parts of ethyl 4-[(4-chlorophenyl)amino]-1-piperidinecarboxylate, 5.4 parts of N,N-diethylethanamine and 160 parts of benzene is added dropwise 11.07 parts of 4-methoxybenzeneacetyl chloride at a temperature between 32° to 40° C. After the addition is complete, the whole is stirred and refluxed for 3 hours. The reaction mixture is cooled and filtered. The filtrate is washed successively with water, sodium hydrogen carbonate solution and water, dried, filtered and evaporated in vacuo. The oily residue is crystallized from a mixture of 56 parts of 1,1'-oxybisethane and 40 parts of hexane. The crude solid product is filtered off and recrystallized from a mixture of benzene and 1,1'-oxybisethane, yielding 3 parts of ethyl 4-{N-(4-chlorophenyl)-N-[(4-methoxyphenyl)acetyl]amino}-1-piperidinecarboxylate; mp. 137° C.

EXAMPLE XVII

A mixture of 20 parts of ethyl 4-[N-(2-chlorophenyl)-N-(phenylacetyl)amino]-1-piperidinecarboxylate and 300 parts of hydrobromic acid solution 48% is stirred and refluxed for 1h.10. The hydrobromic acid solution 48% is removed in vacuo and to the residue is added successively water and sodium hydroxide solution. The free base is extracted with trichloromethane. The latter is dried and evaporated. The solid residue is washed with 1,1'-oxybisethane and dried, yielding 10.6 parts of N-(2-chlorophenyl)-N-(4-piperidinyl)benzeneacetamide; mp. 135.5° C.

EXAMPLE XVIII

Following the procedure of Example XVII and using and equivalent amount of an appropriate ethyl 4-[N-aryl-N-(arylacetyl)amino]-1-piperidinecarboxylate in place of the ethyl 4-[N-(2-chlorophenyl)-N-(phenylacetyl)amino]-1-piperidinecarboxylate used therein, the following compounds are obtained:

| Ar | Ar¹ | mp. |
|---|---|---|
| 2-Cl, 6-CH₃—C₆H₃ | C₆H₅ | 157° C. |
| 4-F—C₆H₄ | C₆H₅ | 96.5° C. |
| 3,4-(Cl)₂—C₆H₃ | C₆H₅ | 81° C. |
| 3-Cl—C₆H₄ | C₆H₅ | 110.5° C. |
| 4-Cl—C₆H₄ | 4-F—C₆H₄ | 109° C. |
| 4-Cl—C₆H₄ | 3-CH₃—C₆H₄ | 104.5° C. |
| 4-Br—C₆H₄ | C₆H₅ | 121.5° C. |
| 4-Cl—C₆H₄ | 2-Cl—C₆H₄ | 72.9° C. |
| 4-Cl—C₆H₄ | 3-Cl—C₆H₄ | 64° C. |
| 2-Cl, 6-CH₃—C₆H₃ | 4-Cl—C₆H₄ | 120.7° C. |
| 4-Cl—C₆H₄ | 2,6-(CH₃)₂—C₆H₃ | 147.3° C. |
| 3,4-(Cl)₂—C₆H₃ | 4-Cl—C₆H₄ | 98.7° C. |
| 2,5-(Cl)₂—C₆H₃ | 4-Cl—C₆H₄ | 125.6° C. |
| 2,6-(Cl)₂—C₆H₃ | 4-Cl—C₆H₄ | 126.3° C. |

EXAMPLE XIX

A mixture of 5 parts of ethyl 4-[N-(2,6-dimethylphenyl)-N-(phenylacetyl)amino]-1-piperidinecarboxylate in 60 parts of hydrobromic acid solution 48% is warmed until the evolution of carbon dioxide is ceased. Heating is continued for 15 minutes at a temperature between 80°-120° C. The reaction mixture is evaporated. The solid residue is washed successively with methylbenzene and 2-propanone and dried, yielding 4.1 parts of N-(2,6-dimethylphenyl)-N-(4-piperidinyl)benzeneacetamide hydrobromide; mp. 251.5° C.

EXAMPLE XX

A mixture of 10 parts of ethyl 4-[N-(4-chlorophenyl)-N-(phenylacetyl)amino]-1-piperidinecarboxylate and 125 parts of glacial acetic acid, previously saturated with gaseous hydrogen bromide, is heated for 9h.45 at 62° C., while stirring. The reaction mixture is cooled and glacial acetic acid is evaporated in vacuo. The semi-solid residue is taken up in 150 parts of water, alkalized with a concentrated sodium hydroxide solution and the product is extracted with trichloromethane. The extract is dried over sodium sulfate and evaporated. The oily residue is triturated in 56 parts of 1,1′-oxybisethane and the solid crude free base is filtered off. It is converted into the hydrochloride salt in the conventional manner in 1,1′-oxybisethane and 2-propanone, yielding 4 parts of N-(4-chlorophenyl)-N-(4-piperidinyl)benzeneacetamide hydrochloride; mp. 206.5° C.

EXAMPLE XXI

Following the procedure of Example XX and using an equivalent amount of an appropriate ethyl 4-[N-aryl-N-(arylacetyl)amino]-1-piperidinecarboxylate as a starting material, the following compounds are prepared:

N-(2,6-dimethylphenyl)-N-(4-piperidinyl)-2-thiopheneacetamide; mp. 128° C.;
N-(4-chlorophenyl)-N-(4-piperidinyl)-2-thiopheneacetamide hydrochloride; mp. 201.5° C.;
4-chloro-N-(4-chlorophenyl)-N-(4-piperidinyl)-4-benzeneacetamide hydrochloride; mp. 222° C.; and
N-(4-chlorophenyl)-4-methyl-N-(4-piperidinyl)benzeneacetamide; mp. 121° C.

EXAMPLE XXII

To a stirred and refluxing mixture of 48 parts of 1-(1-methylethyl)-4-piperidinone, 1 part of 4-methylbenzenesulfonic acid and 540 parts of methylbenzene is added dropwise a solution of 30 parts of benzenamine in 90 parts of methylbenzene. Upon completion, the whole is stirred and refluxed for 3 hours with water-separator. The reaction mixture is evaporated, yielding 72 parts of N-[1-(1-methylethyl)-4-piperidinylidene]benzenamine as a residue.

To a stirred and warmed (30°–40° C.) solution of 72 parts of N-[1-(1-methylethyl)-4-piperidinylidene]benzenamine in 480 parts of methanol are added portionwise 20 parts of sodium borohydride. Upon completion, stirring is continued overnight at at room temperature. The reaction mixture is evaporated and the residue is dissolved in water. The solution is extracted with 4-methyl-2-pentanone. The extract is washed with water and acidified with a diluted hydrochloric acid solution. The aqueous acid phase is alkalized with a diluted sodium hydroxide solution till pH 9 and the product is extracted with 4-methyl-2-pentanone. The extract is washed with water, dried, filtered and evaporated. The residue is distilled (bp. 135°–140° C. at 0.2 mm. pressure) and the distillate is crystallized from petroleumether, yielding 21 parts of 1-(1-methylethyl)-N-phenyl-4-piperidinamine; mp. 69.3° C.

EXAMPLE XXIII

To a warm (40° C.) solution of 12 parts of potassium hydroxide in 240 parts of 2-propanol are added at once 21 parts of ethyl 4-{N-(4-chlorophenyl)-N-[(4-methoxyphenyl)acetyl]amino}-1-piperidinecarboxylate and the whole is stirred and refluxed for 21 hours. The reaction mixture is cooled, filtered and the filtrate is evaporated. The residue is taken up in water and the aqueous solution is acidified with diluted hydrochloric acid solution. The acid solution is washed with 1,1′-oxybisethane, alkalized with sodium hydroxide and the free base is extracted with methylbenzene. The latter is dried, filtered and evaporated. The residue is dissolved in 1,1′-oxybisethane and after crystallization, 10 parts of N-(4-chlorophenyl)-4-methoxy-N(4-piperidinyl)benzeneacetamide are obtained; mp. 129.5° C.

EXAMPLE XXIV

To a stirred and warm (40° C.) solution of 12 parts of potassium hydroxide in 200 parts of 2-propanol are added at once 21 parts of ethyl 4-{N-(4-chlorophenyl)-N-[(3-methoxyphenyl)acetyl]-amino}-1-piperidinecarboxylate and the whole is stirred and refluxed for 17 hours. The reaction mixture is cooled, filtered and evaporated. The semi-solid residue is acidified with a diluted hydrochloric acid solution, washed with 1,1′-oxybisethane and the aqueous acid phase is alkalized with sodium hydroxide solution. The free base is extracted with trichloromethane. The extract is dried and evaporated. The residue is crystallized from a mixture of 1,1′-oxybisethane and hexane, yielding 7.8 parts of N-(4-chlorophenyl)-3-methoxy-N-(4-piperidinyl)benzeneacetamide; mp. 85.7° C.

EXAMPLE XXV

A mixture of 52 parts of 2-bromopropane, 19 parts of N-(4-piperidinyl)-3-pyridinamine, 33.3 parts of sodium carbonate, 3 parts of potassium iodide and 720 parts of 4-methyl-2-pentanone is stirred and refluxed for 24 hours. The reaction mixture is cooled and filtered. The filtrate is evaporated. The residue is purified by column-chromatography over silica gel using methanol as eluent. The pure fractions are collected and the eluent is evaporated. The residue is crystallized from 2,2′-oxybispropane, yielding 1.5 parts of N-[1-(1-methylethyl)-4-piperidinyl]-3-pyridinamine; mp. 100.7° C.

EXAMPLE XXVI

Following the procedure of Example XXV and using equivalent amounts respectively of an appropriate bromide and of an appropriate 4-(arylamino)-4-X-piperidine as starting materials and carrying out the reaction in the indicated solvent, the following compounds are obtained in free base form or in hydrochloride salt form after treatment with hydrochloric acid:

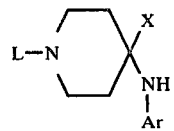

| L | Ar | X | base or salt form | mp. | Solvent |
|---|---|---|---|---|---|
| $(CH_3)_2$—CH— | $C_6H_5$ | $COOC_2H_5$ | 2 HCl . $H_2O$ | 148.6° C. | MIK |
| $(CH_3)_2$—CH— | $C_6H_5$ | $COOCH_3$ | 2 HCl ½ $H_2O$ | 168.7° C. | MIK |

-continued

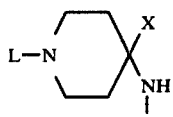

| L | Ar | X | base or salt form | mp. | Solvent |
|---|---|---|---|---|---|
| cyclopentyl | 3-pyridinyl | H | base | 134° C. | MIK |
| cyclopentyl | 2-pyridinyl | H | base | 143.7° C. | MIK |
| cyclopentyl | C$_6$H$_5$ | COOC$_2$H$_5$ | 2 HCl | 195.4° C. | MIK |
| cyclopentyl | C$_6$H$_5$ | COOCH$_3$ | 2 HCl | 195.4° C. | MIK |
| cyclohexyl | C$_6$H$_5$ | H | 2 HCl | — | MIK |
| (CH$_3$)$_2$—CH— | 2-pyridinyl | H | base | 93.5° C. | butanol |
| (CH$_3$)$_2$—CH— | 2,6-(CH$_3$)$_2$—C$_6$H$_3$ | H | base | <50° C. | butanol |
| cyclopentyl | C$_6$H$_5$ | H | 2 HCl | 259.3° C. | butanol |

EXAMPLE XXVII

To a stirred mixture of 15 parts of N-(4-chlorophenyl)-4-piperidinamine, 12 parts of N,N-diethylethanamine in 130 parts of benzene is added dropwise a solution of 10.3 parts of 3-bromo-1-propene in 70 parts of benzene. Upon completion, the whole is stirred first for 20h.30 at room temperature and further for 40 minutes at reflux. The reaction mixture is cooled, filtered and the filtrate is evaporated. The residue is taken up in 1,1'-oxybisethane and treated with activated charcoal. The latter is filtered off and the 1,1'-oxybisethane is evaporated again, yielding 2.9 parts of N-(4-chlorophenyl)-1-(2-propenyl)-4-piperidinamine; mp. 90° C.

EXAMPLE XXVIII

To a warm (about 40° C.) and stirred mixture of 5 parts of N-(2,6-dimethylphenyl)-4-piperidinamine, 5 parts of sodium carbonate, a few crystals of potassium iodide in 120 parts of benzene is added dropwise a solution of 5.1 parts of 1-iodopropane in 80 parts of benzene. After the addition is complete, stirring is continued for 40 hours at reflux temperature. The reaction mixture is cooled and 50 parts of water are added. The organic layer is separated, dried and evaporated in vacuo. The oily residue is distilled, yielding 10.2 parts of N-(2,6-dimethylphenyl)-1-propyl-4-piperidinamine; bp. 135° C. at 0.2 mm. pressure.

EXAMPLE XXIX

To 0.5 parts of a solution of 2 parts of thiophene in 40 parts of ethanol, are added 2 parts of cyclopentanone, 5.5 parts of N-(4-piperidinyl)-2-pyrimidinamine and 120 parts of methanol. The whole is hydrogenated at normal pressure and at room temperature with 2 parts of palladium-on-charcoal 10%. After the calculated amount of hydrogen is taken up, the catalyst is filtered off and the filtrate is evaporated. The residue is taken up in 4-methyl-2-pentanone and a small amount of trichloromethane. The whole is washed twice with a diluted sodium hydroxide solution, dried, filtered and evaporated. The residue is crystallized from 2,2'-oxybispropane. The product is filtered off and dried, yielding 2.3 parts of N-(1-cyclopentyl-4-piperidinyl)-2-pyrimidinamine; mp. 118° C.

EXAMPLE XXX

To 0.5 parts of solution of 2 parts of thiophene in 40 parts of ethanol, are added 4 parts of 2-propanone, 4.5 parts of N-(4-piperidinyl)-2-pyrimidinamine and 120 parts of methanol. The whole is hydrogenated at normal pressure and at room temperature with 2 parts of palladium-on-charcoal catalyst 10%. After the calculated amount of hydrogen is taken up, the catalyst is filtered off and the filtrate is evaporated. The residue is dissolved in trichloromethane. The solution is washed successively with a diluted sodium hydroxide solution and with water, dried, filtered and evaporated, yielding 3 parts of N-[1-(1-methylethyl)-4-piperidinyl]-2-pyrimidinamine as a residue.

EXAMPLE XXXI

To a stirred and refluxing suspension of 2 parts of lithium aluminiumhydride in 120 parts of 1,1'-oxybisethane is added dropwise a solution of 13 parts of ethyl 4-[N-(2,6-dimethylphenyl)amino]-1-piperidinecarboxylate in 40 parts of 1,1'-oxybisethane. After the addition is complete, stirring and refluxing is continued for 20 hours. The reaction mixture is cooled to 5° C. and 7 parts of water are added. The formed precipitate is filtered off, washed on the filter with 1,1'-oxybisethane and the filtrate is evaporated. The oily residue is distilled, yielding 5.8 parts of N-(2,6-dimethylphenyl)-1-methyl-4-piperidinamine; bp. 90°–93° C. at 0.003 mm. pressure. On standing the distillate solidifies, to yield solid N-(2,6-dimethylphenyl)-1-methyl-4-piperidinamine with a melting point of 45° C.

EXAMPLE XXXII

To a stirred suspension of 5 parts of N-(4-chlorophenyl)-N-(4-piperidinyl)benzeneacetamide, 5 parts of sodium carbonate, a few crystals of potassium iodide in 200 parts of butanol is added dropwise 4 parts of 2-bromopropane at room temperature. After the addition is complete, the whole is stirred and refluxed for 20 hours. Then the second portion of 4 parts of 2-bromopropane is added and stirring and refluxing is continued for another 19 hours. The reaction mixture is cooled, filtered and the filtrate is evaporated. From the oily free base, the hydrochloride salt is prepared in the conventional manner in 1,1'-oxybisethane and 2-propanone. The precipitated solid salt is filtered off and crystallized from a mixture of 2-propanone and 2-propanol, yielding 2 parts of N-(4-chlorophenyl)-N-[1-(1-methylethyl)-4-piperidinyl]benzeneacetamide hydrochloride; mp. 263° C.

EXAMPLE XXXIII

Following the procedure of Example XXXII and using an equivalent amount of an appropriate bromide and of an appropriate N-aryl-N-(4-piperidinyl)arylacetamide as starting materials, the following compounds are prepared in hydrochloride salt form:

| L | Ar | Ar$^1$ | Salt form | mp. |
|---|---|---|---|---|
| $(CH_3)_2$—CH— | 4-Cl—$C_6H_4$ | 2-thienyl | HCl | 273.5° C. |
| $(CH_3)_2$—CH— | 2,6-$(CH_3)_2$—$C_6H_3$ | $C_6H_5$ | HCl | 292° C. |
| $(CH_3)_2$—CH— | 2,6-$(CH_3)_2$—$C_6H_3$ | 2-thienyl | HCl | 230.5° C. |
| $(CH_3)_2$—CH— | 4-Cl—$C_6H_4$ | 4-$CH_3$—$C_6H_4$ | HCl | 279° C. |
| $(CH_3)_2$—CH— | 2-Cl, 6-$CH_3$—$C_6H_3$ | $C_6H_5$ | HCl | 266.5° C. |
| $(CH_3)_2$—CH— | 4-Cl—$C_6H_4$ | 4-$OCH_3$—$C_6H_4$ | HCl . $H_2O$ | 264° C. |
| $(CH_3)_2$—CH— | 3,4-$(Cl)_2$—$C_6H_3$ | $C_6H_5$ | HCl | 262.5° C. |
| $(CH_3)_2$—CH— | 3-Cl—$C_6H_4$ | $C_6H_5$ | HCl | 221.5° C. |
| $(CH_3)_2$—CH— | 4-Cl—$C_6H_4$ | 4-F—$C_6H_4$ | HCl | 270.5° C. |
| $(CH_3)_2$—CH— | 4-Cl—$C_6H_4$ | 3-$CH_3$—$C_6H_4$ | HCl | 261.5° C. |
| $(CH_3)_2$—CH— | 3,4-$(Cl)_2$—$C_6H_3$ | 4-Cl—$C_6H_4$ | HCl | 268.6° C. |
| n-$C_4H_9$— | 4-Cl—$C_6H_4$ | $C_6H_5$ | HCl | 224° C. |
| $CH_3$—$CH_2$—$CH(CH_3)$— | 4-Cl—$C_6H_4$ | $C_6H_5$ | HCl | 245.5° C. |
| $CH_3$—$CH(CH_3)$—$CH_2$—$CH_2$— | 4-Cl—$C_6H_4$ | $C_6H_5$ | HCl | 225.5° C. |
| n$C_6H_{13}$— | 4-Cl—$C_6H_4$ | $C_6H_5$ | HCl | 177.5° C. |
| n$C_7H_{15}$— | 4-Cl—$C_6H_4$ | $C_6H_5$ | HCl | 157.5° C. |
| n$C_{10}H_{21}$— | 4-Cl—$C_6H_4$ | $C_6H_5$ | HCl | 138.5° C. |
| cyclopentyl— | 4-Cl—$C_6H_4$ | 4-$CH_3$—$C_6H_4$ | HCl | 276.8° C. |
| cyclohexyl— | 4-Cl—$C_6H_4$ | $C_6H_5$ | HCl | 274° C. |

EXAMPLE XXXIV

To a stirred and warm (40° C.) mixture of 5 parts of N-(4-chlorophenyl)-N-(4-piperidinyl)benzeneacetamide, 5 parts of sodium carbonate, a few crystals of potassium iodide and 200 parts of n.butanol is added 3.75 parts of bromocyclopentane and the whole is stirred and refluxed for 21h. 30. Then a second portion of 5 parts of bromocyclopentane is added and stirring at reflux temperature is continued for another 30 hours. The reaction mixture is cooled, filtered and the filtrate is evaporated. The oily residue solidifies on triturating in 1,1'-oxybisethane. The solid product is filtered off and crystallized from 1,1'-oxybisethane, yielding 1.1 parts of N-(4-chlorophenyl)-N-(1-cyclopentyl-4-piperidinyl)benzeneacetamide; mp. 139.5° C.

EXAMPLE XXXV

Following the procedure of Example XXXIV and using equivalent amounts respectively of an appropriate bromide and of an appropriate N-aryl-N-(4-piperidinyl)arylacetamide as starting materials, the following compounds are obtained:

| L | Ar | Ar$^1$ | mp. |
|---|---|---|---|
| $(CH_3)_2$—CH— | 4-F—$C_6H_4$ | $C_6H_5$ | 108.5° C. |
| $(CH_3)_2$—CH— | 4-Cl—$C_6H_4$ | 4-Cl—$C_6H_4$ | 106.5° C. |
| $(CH_3)_2$—CH— | 4-Br—$C_6H_4$ | $C_6H_5$ | 97° C. |
| $(CH_3)_2$—CH— | 4-Cl—$C_6H_4$ | 2-Cl—$C_6H_4$ | 143.2° C. |

-continued

| L | Ar | Ar¹ | mp. |
|---|---|---|---|
| $(CH_3)_2$—CH— | 4-Cl—$C_6H_4$ | 3-$OCH_3$—$C_6H_4$ | 96.4° C. |
| $(CH_3)_2$—CH— | 4-Cl—$C_6H_4$ | 3-Cl—$C_6H_4$ | 61.6° C. |
| $(CH_3)_2$—CH— | 2-Cl,6-$CH_3$—$C_6H_3$ | 4-Cl—$C_6H_4$ | 94.2° C. |
| $(CH_3)_2$—CH— | 4-Cl—$C_6H_4$ | 2,6-$(CH_3)_2$—$C_6H_3$ | 126.6° C. |
| $(CH_3)_2$—CH— | 2,5-$(Cl)_2$—$C_6H_3$ | 4-Cl—$C_6H_4$ | 102.5° C. |
| $(CH_3)_2$—CH— | 2,6-$(Cl)_2$—$C_6H_3$ | 4-Cl—$C_6H_4$ | 129.1° C. |
| $(CH_3)_2$—CH— | 2-Cl—$C_6H_4$ | $C_6H_5$ | 87.5° C. |
| cyclopropyl-CH₂— | 4-Cl—$C_6H_4$ | 4-Cl—$C_6H_4$ | 133.1° C. |
| cyclopropyl-CH₂— | 4-Cl—$C_6H_4$ | 2-Cl—$C_6H_4$ | 128.6° C. |
| cyclopropyl-CH₂— | 4-Cl—$C_6H_4$ | 3-$OCH_3$—$C_6H_4$ | 157.5° C. |
| cyclopropyl-CH₂— | 4-Cl—$C_6H_4$ | 3-$CH_3$—$C_6H_4$ | 155° C. |
| cyclopropyl-CH₂— | 4-Cl—$C_6H_4$ | 4-F—$C_6H_4$ | 143.5° C. |

EXAMPLE XXXVI

To a stirred and refluxing mixture of 5 parts of N-(4-chlorophenyl)-N-(4-piperidinyl)benzeneacetamide, 5 parts of sodium hydrogen carbonate and 200 parts of benzene are added portionwise 6.7 parts of (bromomethyl)cyclopropane and stirring and refluxing is continued for 23 hours. The reaction mixture is cooled and filtered. The filtrate is evaporated. The semi-solid residue is dissolved in a mixture of benzene and 1,1'-oxybisethane. The precipitated impurities are filtered off and the filtrate is evaporated again. From the oily free base, the hydrochloride salt is prepared in the conventional manner, yielding, after crystallization of the crude salt from a mixture of trichloromethane and 1,1'-oxybisethane, 1.5 parts of N-(4-chlorophenyl)-N-[1-(cyclopropylmethyl)-4-piperidinyl]benzeneacetamide hydrochloride; mp. 224° C.

EXAMPLE XXXVII

To a stirred solution of 5 parts of N-(4-chlorophenyl)-N-(4-piperidinyl)benzeneacetamide, 3.8 parts of N,N-diethylethanamine in 200 parts of benzene are added portionwise 5 parts of 3-bromo-1-propene. After the addition is complete, the whole is heated for 21 hours at a temperature between 50°–60° C. The reaction mixture is cooled and filtered. The filtrate is washed successively with water, sodium hydrogen carbonate solution and water, dried over potassium carbonate and evaporated. The oily residue is converted into the hydrochloride salt in 1,1'-oxybisethane and 2-propanone, yielding 4 parts of N-(4-chlorophenyl)-N-[1-(2-propenyl)-4-piperidinyl]benzeneacetamide hydrochloride; mp. 225.5° C.

EXAMPLE XXXVIII

Following the procedure of Example XXXVII and using an equivalent amount of an appropriate N-aryl-N-(4-piperidinyl)-arylacetamide in place of the N-(4-chlorophenyl)-N-(4-piperidinyl)-benzeneacetamide used therein, the following compounds are prepared:

N-(2,6-dimethylphenyl)-N-[1-(2-propenyl)-4-piperidinyl]-2-thiopheneacetamide hydrochloride; mp. 203.5° C. and N-(2,6-dimethylphenyl)-N-[1-(2-propenyl)-4-piperidinyl]benzeneacetamide hydrochloride; mp. 214° C.

EXAMPLE XXXIX

To a warm suspension of 5 parts of N-(4-chlorophenyl)-N-(4-piperidinyl)benzeneacetamide, 5 parts of sodium carbonate, a few crystals of potassium iodide in 200 parts of n, butanol is added 4 parts of 2-chloro-2-methylpropane at a temperature of 30°–40° C. The whole is stirred and refluxed for 140 hours during which time, 35 parts of 2-chloro-2-methylpropane are added in portions as follows: after a reflux-time of 15 hours, 4 parts of 2-chloro-2-methylpropane is added, after 8 hours, 10 parts, after 16 hours, 11 parts and finally after 47 hours, 10 parts. The reaction mixture is cooled, filtered and the filtrate is evaporated. The semi-solid residue is dissolved in a mixture of methylbenzene, dimethoxyethane and 1,1'-oxybisethane. The solution is filtered from some impurities and the filtrate is evaporated again. From the oily residue, the hydrochloride salt is prepared in the conventional manner in 1,1'-oxybisethane, yielding, after recrystallization of the crude solid salt from 2-propanone, 0.9 parts of N-(4-chlorophenyl)-N-[1-(1,1-dimethylethyl)-4-piperidinyl]benzeneacetamide hydrochloride; mp. 221° C.

EXAMPLE XL

A mixture of 4 parts of iodoethane, 5 parts of N-(2,6-dimethylphenyl)-N-(4-piperidinyl)benzeneacetamide, 5 parts of sodium carbonate, a few crystals of potassium iodide in 200 parts of benzene is stirred and refluxed for 23 hours. The reaction mixture is filtered hot and the filtrate is evaporated in vacuo. The solid residue is crystallized from 1,1'-oxybisethane, yielding 2 parts of N-(2,6-dimethylphenyl)-N-(1-ethyl-4-piperidinyl)-benzeneacetamide; mp. 86.5° C.

EXAMPLE XLI

Following the procedure of Example XL and using an equivalent amount of an appropriate N-aryl-N-(4-piperidinyl)-arylacetamide in place of the N-(2,6-dimethylphenyl)-N-(4-piperidinyl)benzeneacetamide used therein, the following compounds are prepared:

2-chloro-N-(4-chlorophenyl)-N-(1-ethyl-4-piperidinyl)-benzeneacetamide hydrochloride; mp. 234.6° C.;

N-(4-chlorophenyl)-N-(1-ethyl-4-piperidinyl)-3-methylbenzeneacetamide; mp. 78.5° C.;

N-(4-chlorophenyl)-N-(1-ethyl-4-piperidinyl)-4-methylbenzeneacetamide; mp. 50° C.; and N-(4-chlorophenyl)-N-(1-ethyl-4-piperidinyl)-4-fluorobenzeneacetamide; mp. 62.3° C.

EXAMPLE XLII

To a stirred and refluxing mixture of 5 parts of 4-chloro-N-(4-chlorophenyl)-N-(4-piperidinyl)benzeneacetamide, 5 parts of sodium carbonate, 0.4 parts of potassium iodide and 200 parts of butanol is added 4.7 parts of 1-iodopropane and the whole is stirred and refluxed for 22 hours. Then a second portion of 4.5 parts of 1-iodopropane is added and stirring and refluxing is continued for 27h.30. The reaction mixture is cooled, filtered and the filtrate is evaporated. The semi-solid residue is dissolved in methylbenzene. The solution is filtered from some impurities and the filtrate is evaporated again. The residue is crystallized from 1,1'-oxybisethane at −10° C., yielding 0.9 parts of 4-chloro-N-(4-chlorophenyl)-N-(1-propyl-4-piperidinyl)benzeneacetamide; mp. 118.6° C.

EXAMPLE XLIII

To a stirred solution of 4 parts of N-(4-chlorophenyl)-N-(4-piperidinyl)benzeneacetamide and 3 parts of N,N-diethylethanamine in 200 parts of benzene are added portionwise 4 parts of 1-iodopropane and the whole is stirred and refluxed for 47 hours. Then the second portion of 4 parts of 1-iodopropane is added and stirring and refluxing is continued for another 20h.20. The reaction mixture is cooled and filtered. The filtrate is washed with water, dried and evaporated in vacuo. From the oily free base, the hydrochloride salt is prepared in the conventional manner in 1,1'-oxybisethane. The precipitated solid salt is filtered off and dried, yielding 3.5 parts of N-(4-chlorophenyl)-N-(1-propyl-4-piperidinyl)benzeneacetamide hydrochloride; mp. 233.5° C.

EXAMPLE XLIV

Following the procedure of Example XLIII and using an equivalent amount respectively of an appropriate iodoalkane and of an appropriate N-aryl-N-(4-piperidinyl)arylacetamide in place of the 1-iodopropane and the N-(4-chlorophenyl)-N-(4-piperidinyl)benzeneacetamide used therein, the following compounds are obtained:

N-(2,6-dimethylphenyl)-N-(1-ethyl-4-piperidinyl)-2-thiopheneacetamide hydrochloride; mp. 258° C.;
N-(4-chlorophenyl)-N-(1-ethyl-4-piperidinyl)-2-thiopheneacetamide hydrochloride; mp. 220.5° C.;
N-(4-chlorophenyl)-N-(1-ethyl-4-piperidinyl)benzeneacetamide hydrochloride; mp. 215° C.;
4-chloro-N-(4-chlorophenyl)-N-(1-ethyl-4-piperidinyl)benzeneacetamide hydrochloride; mp. 224° C.; and
N-(4-chlorophenyl)-N-(1-propyl-4-piperidinyl)-2-thiopheneacetamide; mp. 241° C.

EXAMPLE XLV

A mixture of 4.5 parts of N-(1-cyclopentyl-4-piperidinyl)-2-pyrimidinamine, 3.4 parts of 3-methylbenzeneacetyl chloride, 2 parts of sodium carbonate and 180 parts of dimethylbenzene is stirred and refluxed for 17 hours. Another 9 parts of 3-methylbenzeneacetyl chloride is added dropwise. Upon completion, stirring is continued for 67 hours at reflux temperature. The reaction mixture is cooled, water is added and the layers are separated. The organic phase is extracted with a diluted hydrochloric acid solution. The combined aqueous phases are washed with benzene and alkalized with a diluted sodium hydroxide solution while cooling in an ice-bath. The product is extracted twice with trichloromethane. The combined extracts are dried, filtered and evaporated. The residue is converted into the ethanedioate salt in 2-propanol. The salt is filtered off and crystallized twice first from ethanol and then from methanol, yielding 1 part of N-(1-cyclopentyl-4-piperidinyl)-3-methyl-N-(2-pyrimidinyl)benzeneacetamide ethanedioate; mp. 204.1° C.

EXAMPLE XLVI

Following the procedure of Example XLV and using equivalent amounts respectively of an appropriate N-aryl-4-piperidinamine and of an appropriate arylacetyl chloride as starting materials, the following compounds are obtained in base form or in the form of an acid addition salt after treatment with the appropriate acid:

| L | Ar | Ar¹ | base or salt form | mp. |
|---|---|---|---|---|
|  | 3-pyridinyl | $C_6H_5$ | (E)-2-butenedioate | 219.6° C. |
| 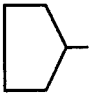 | 3-pyridinyl | $3\text{-}CH_3\text{-}C_6H_4$ | (E)-2-butenedioate | 250.3° C. |
| 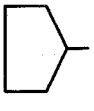 | 2-pyridinyl | $3\text{-}Cl\text{-}C_6H_4$ | $(COOH)_2$ | 205.9° C. |
| 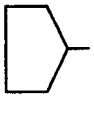 | 2-pyridinyl | $3\text{-}CH_3\text{-}C_6H_4$ | base | 107.8° C. |

-continued

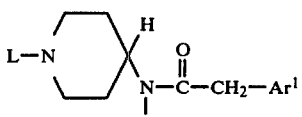

| L | Ar | Ar¹ | base or salt form | mp. |
|---|---|---|---|---|
| ⌊▷ | 2-pyridinyl | 4-Cl—C₆H₄ | base | 119.2° C. |
| ⌊▷ | 2-pyridinyl | 2-thienyl | base | 129.4° C. |
| ⌊▷ | 2-pyridinyl | C₆H₅ | base | 108.8° C. |
| ⌊▷ | 2-pyrimidinyl | C₆H₅ | (COOH)₂ | 223.5° C. |
| (CH₃)₂—CH— | 3-pyridinyl | C₆H₅ | base | 129.4° C. |
| (CH₃)₂—CH— | 3-pyridinyl | 3-Cl—C₆H₄ | base | 117.7° C. |
| (CH₃)₂—CH— | 3-pyridinyl | 4-Cl—C₆H₄ | base | 146.6° C. |
| (CH₃)₂—CH— | 3-pyridinyl | 2-thienyl | base | 126.7° C. |
| (CH₃)₂—CH— | 3-pyridinyl | 3-CH₃—C₆H₄ | base | 100° C. |
| (CH₃)₂—CH— | 2-pyridinyl | 3-Cl—C₆H₄ | base | 102.6° C. |
| (CH₃)₂—CH— | 2-pyridinyl | C₆H₅ | base | 72.1° C. |
| (CH₃)₂—CH— | 2-pyridinyl | 4-Cl—C₆H₄ | base | 83.3° C. |
| (CH₃)₂—CH— | 2-pyridinyl | 3-CH₃—C₆H₄ | (COOH)₂ | 190.6° C. |
| (CH₃)₂—CH— | 2-pyridinyl | 2-thienyl | (COOH)₂ | 196.1° C. |
| (CH₃)₂—CH— | 2-pyrimidinyl | 4-Cl—C₆H₄ | (COOH)₂ | 195.7° C. |

EXAMPLE XLVII

A mixture of 5 parts of methyl 1-(1-methylethyl)-4-(phenylamino)-4-piperidinecarboxylate, 24 parts of 4-chlorobenzeneacetyl chloride, 4 parts of sodium carbonate and 180 parts of dimethylbenzene is stirred and refluxed for 32 hours. The reaction mixture is cooled, washed with a diluted sodium hydroxide solution and extracted with a diluted hydrochloric acid solution: three layers are obtained. The oil and the aqueous phase are combined and alkalized with a diluted sodium hydroxide solution. The product is extracted with 4-methyl-2-pentanone. The extract is washed with water, dried, filtered and evaporated. The residue is converted into the ethanedioate salt in 2-propanol. The salt is filtered off and crystallized from a mixture of 2-propanol and 2,2'-oxybispropane, yielding 5 parts (48%) of methyl 4-[N-(4-chlorophenyl)acetyl-N-phenylamino]-1-(1-methylethyl)-4-piperidinecarboxylate ethanedioate; mp. 154.2° C.

EXAMPLE XLVIII

Following the procedure of Example XLVII and using equivalent amounts respectively of an appropriate 4-arylamino-4-piperidinecarboxylate and of an appropriate arylacetyl chloride as starting materials, the following compounds are obtained in free base form or in the form of an acid addition salt after treatment with the appropriate acid:

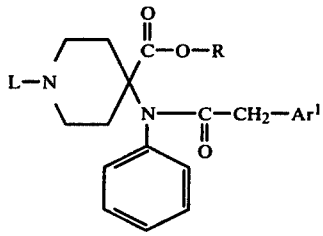

| L | Ar¹ | R | base or salt form | mp. |
|---|---|---|---|---|
| (CH₃)₂—CH— | 3-CH₃—C₆H₄ | C₂H₅ | (COOH)₂ | 198.4° C. |
| (CH₃)₂—CH— | C₆H₅ | C₂H₅ | (E)-2-butenedioate | 168.5° C. |
| (CH₃)₂—CH— | 2-thienyl | C₂H₅ | (COOH)₂ | 156.8° C. |
| (CH₃)₂—CH— | 4-Cl—C₆H₄ | C₂H₅ | HCl | 191.5° C. |
| (CH₃)₂—CH— | 3-CH₃—C₆H₄ | CH₃ | (COOH)₂ | 170° C. |
| (CH₃)₂—CH— | 3-Cl—C₆H₅ | CH₃ | (COOH)₂ | 152.2° C. |
| (CH₃)₂—CH— | C₆H₅ | CH₃ | (COOH)₂ | 165.5° C. |
| (CH₃)₂—CH— | 2-thienyl | CH₃ | (COOH)₂ | 173.6° C. |
|  | 4-Cl—C₆H₄ | C₂H₅ | (E)-2-butenedioate | 195.6° C. |
|  | C₆H₅ | C₂H₅ | (E)-2-butenedioate | 203.3° C. |
|  | 3-Cl—C₆H₄ | C₂H₅ | (E)-2-butenedioate | 207.8° C. |

-continued

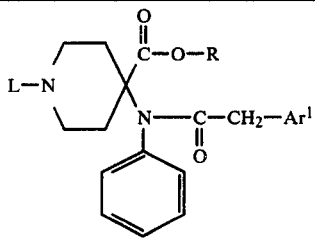

| L | Ar¹ | R | base or salt form | mp. |
|---|---|---|---|---|
| cyclopropylmethyl | 3-CH₃—C₆H₄ | C₂H₅ | (E)-2-butenedioate | 188.1° C. |
| cyclopropylmethyl | C₆H₅ | CH₃ | (COOH)₂ | 197.2° C. |
| cyclopropylmethyl | 2-thienyl | CH₃ | (COOH)₂ | 166.4° C. |
| cyclopropylmethyl | 3-Cl—C₆H₄ | CH₃ | base | 94° C. |
| cyclopropylmethyl | 3-CH₃—C₆H₄ | CH₃ | (COOH)₂ | 189.5° C. |

EXAMPLE IL

To a stirred mixture of 4.4 parts of 1-(1-methylethyl)-N-phenyl-4-piperidinamine, 5.3 parts of sodium carbonate and 180 parts of benzene are added dropwise 5 parts of benzeneacetyl chloride. Upon completion, stirring is continued overnight at reflux. The reaction mixture is cooled, washed successively with water, a sodium hydrogen carbonate solution and again with water, dried, filtered and evaporated. The residue is converted into the hydrochloride salt in 2,2'-oxybispropane and 2-propanol. The formed salt is filtered off and crystallized from a mixture of 2-propanol and 2,2'-oxybispropane, yielding 2.5 parts of N-[1-(1-methylethyl)-4-piperidinyl]-N-phenylbenzeneacetamide hydrochloride; mp. 184.4° C.

EXAMPLE L

Following the procedure of Example IL and using equivalent amounts respectively of an appropriate N-aryl-4-piperdinamine and of an appropriate arylacetyl chloride as starting materials, the following compounds are obtained in base form or in the form of an acid addition salt after treatment with the appropriate acid:

| L | Ar | Ar¹ | base or salt form | mp. |
|---|---|---|---|---|
| (CH₃)₂—CH— | C₆H₅ | 3-CH₃—C₆H₄ | HCl | 173.6° C. |
| (CH₃)₂—CH— | C₆H₅ | 3-Cl—C₆H₄ | HCl | 204.8° C. |
| (CH₃)₂—CH— | C₆H₅ | 2-thienyl | (E)-2-butenedioate | 168.1° C. |
| CH₃ | 2,6-(CH₃)₂—C₆H₃ | C₆H₅ | base | 95.5° C. |
| CH₃ | 4-Cl—C₆H₄ | C₆H₅ | base | 115° C. |
| C₂H₅ | 4-Cl—C₆H₄ | 3-OCH₃—C₆H₄ | base | 90.7° C. |
| nC₃H₇ | 2,6-(CH₃)₂—C₆H₃ | 2-thienyl | (COOH)₂ | 153° C. |
| nC₃H₇ | 2,6-(CH₃)₂—C₆H₃ | C₆H₅ | (COOH)₂ | 161° C. |
| CH₂=CH—CH₂ | 4-Cl—C₆H₄ | 2-thienyl | HCl | 227.5° C. |
| cyclopropylmethyl | C₆H₅ | 4-Cl—C₆H₄ | base | 125.1° C. |
| cyclopropylmethyl | C₆H₅ | 3-CH₃—C₆H₄ | (E)-2-butenedioate | 161.3° C. |
| cyclopropylmethyl | C₆H₅ | 2-thienyl | base | 119° C. |
| cyclopropylmethyl | C₆H₅ | 3-Cl—C₆H₄ | base | 121.8° C. |

-continued

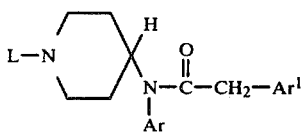

| L | Ar | Ar¹ | base or salt form | mp. |
|---|-----|------|-------------------|-----|
| ⬠ | C$_6$H$_5$ | C$_6$H$_5$ | base | 139.8° C. |
| ⬠ | 3-pyridinyl | 4-Cl—C$_6$H$_4$ | base | 149.9° C. |
| ⬠ | 3-pyridinyl | 3-Cl—C$_6$H$_4$ | 2 HCl . ½H$_2$O | 236.6° C. |
| ⬠ | 3-pyridinyl | 2-thienyl | base | 159.8° C. |
| ⬡H | C$_6$H$_5$ | 4-Cl—C$_6$H$_4$ | HCl | 265.8° C. |
| ⬡H | C$_6$H$_5$ | 3-Cl—C$_6$H$_4$ | HCl | 255.4° C. |

EXAMPLE LI

A suspension of 1.25 parts of sodium amide in 56 parts of benzene is stirred under nitrogen atmosphere and warmed to a temperature of 40° C. Then there is added dropwise a solution of 6 parts of N-(4-chlorophenyl)-1-(1-methylethyl)-4-piperidinamine in 56 parts of benzene. Upon completion, the whole is stirred and refluxed for 16h.45. The mixture is cooled to 25° C. and there is added a mixture of 7.8 parts of 3,4-dichlorobenzeneacetyl chloride in 88 parts of benzene. After stirring and refluxing for 2 additional hours, the reaction mixture is cooled and 80 parts of water are added. The whole is acidified with a diluted hydrochloric acid solution. The aqueous acid phase is alkalized with sodium hydroxide solution and the free base is extracted with trichloromethane. The extract is dried, filtered and evaporated. The residue is dissolved in a mixture of 80 parts of 1,1'-oxybisethane and 120 parts of hexane. The solution is cooled overnight at −10° C., filtered from some impurities and the filtrate is evaporated again. The residue is dissolved in 120 parts of 1,1'-oxybisethane, treated with activated charcoal, filtered and evaporated. The latter residue is crystallized from hexane at −10° C., yielding 2.2 parts of 3,4-dichloro-N-(4-chlorophenyl)-N-[1-(1-methylethyl)-4-piperidinyl]benzeneacetamide; mp. 101.7° C.

EXAMPLE LII

Following the procedure of Example LI and using equivalent amounts respectively of an appropriate N-aryl-4-piperidinamine and of an appropriate arylacetyl chloride as starting materials, the following compounds are obtained in base form or in the form of an acid addition salt after treatment with the appropriate acid:
4-bromo-N-(4-chlorophenyl)-N-[1-(1-methylethyl)-4-piperidinyl]-benzeneacetamide; mp. 118.1° C.;
4-chloro-N-(2,6-dimethylphenyl)-N-[1-(1-methylethyl)-4-piperidinyl]-benzeneacetamide hydrochloride; mp. 268.2° C.; and
N-(4-chlorophenyl)-4-(1-methylethyl)-N-[1-(1-methylethyl)-4-piperidinyl]benzeneacetamide; mp. 104.9° C.

EXAMPLE LIII

5 Parts of 4-chloro-N-(4-chlorophenyl)-N-[1-(1-methylethyl)-4-piperidinyl]benzeneacetamide are dissolved in a mixture of 60 parts of 1,1'-oxybisethane and 16 parts of 2-propanone. The resulting solution is acidified with an excess of 2-propanol previously saturated with gaseous hydrogen chloride. The precipitated salt is filtered off and dried, yielding 7.5 parts of 4-chloro-N-(4-chlorophenyl)-N-[1-(1-methylethyl)-4-piperidinyl]-benzeneacetamide hydrochloride; mp. 266.6° C.

EXAMPLE LIV

From 6 parts of N-[1-(1-methylethyl)-4-piperidinyl]-N-phenyl-2-thiopheneacetamide (E)-2-butenedioate, the free base is liberated in the conventional manner with a diluted sodium hydroxide solution. The product is extracted with trichloromethane. The extract is washed with water, dried, filtered and evaporated. The residue is converted into the ethanedioate salt in 2-propanol. The salt is filtered off and dried, yielding 3.2 parts of N-[1-(1-methylethyl)-4-piperidinyl]-N-phenyl-2-thiopheneacetamide ethanedioate; mp. 167.4° C.

EXAMPLE LV

From an aqueous solution of 2.8 parts of N-(2,6-dimethylphenyl)-N-(1-propyl-4-piperidinyl)-2-thiopheneacetamide dihydrochloride, the free base is liberated by alkalization with sodium hydrogen carbonate solution. The free base is extracted with 1,1'-oxybisethane. The extract is dried and evaporated. The oily residue is dissolved in 56 parts of hexane and after cooling to −10° C., the solid free base is precipitated. It is filtered off and dried, yielding 1.6 parts of N-(2,6-dimethylphenyl)-N-(1-propyl-4-piperidinyl)-2-thiopheneacetamide; mp. 62.5° C.

EXAMPLE LVI

From 3.9 parts of N-(1-cyclopentyl-4-piperidinyl)-3-methyl-N-(3-pyridinyl)benzeneacetamide (E)-2-butenedioate, the free base is liberated in the conventional manner with a diluted sodium hydroxide solution. After extraction with 2,2'-oxybispropane, the latter is washed with water, dried, filtered and evaporated. The residue is converted into the ethanedioate salt in ethanol. The salt is filtered off and crystallized from a mixture of ethanol and 2,2'-oxybispropane, yielding 3 parts of N-(1-cyclopentyl-4-piperidinyl)-3-methyl-N-(3-pyridinyl)-benzeneacetamide ethanedioate; mp. 192.6° C.

EXAMPLE LVII

A mixture of 50 parts of 4-(phenylamino)-1-(phenylmethyl)-4-piperidinecarboxamide and 600 parts of a concentrated hydrochloric acid solution is refluxed for 16 hours. After cooling the reaction mixture is concentrated under diminished pressure to a volume of 400 parts, whereupon a precipitate is formed. It is filtered off, washed with water and 2-propanone and dried, yielding 43 parts of 4-(phenylamino)-1-(phenylmethyl)-4-piperidinecarboxylic acid dihydrochloride; mp. 261°–263° C.(dec.).

A mixture of 19 parts of 4-(phenylamino)-1-(phenylmethyl)-4-piperidinecarboxylic acid dihydrochloride, 14.4 parts of sulfuric acid and 64 parts of ethanol is stirred and refluxed for 16 hours. The solvent is decanted. The residue is dissolved in water. The aqueous solution is alkalized with ammonium hydroxide and extracted with a mixture of methylbenzene and 2,2'-oxybispropane. The combined organic layers are dried over magnesium sulfate, filtered and evaporated. The oily residue is dissolved in 200 parts of 2,2'-oxybispropane and gaseous hydrogen chloride is introduced into the solution. The precipitated hydrochloride is filtered off, washed with 2-propanol, filtered off again and dried, yielding 11.5 parts of ethyl 4-(phenylamino)-1-(phenylmethyl)-4-piperidinecarboxylate dihydrochloride; mp. 212°–214.4° C.

To a stirred and refluxing solution of 101.4 parts of ethyl 4-(phenylamino)-1-(phenylmethyl)-4-piperidinecarboxylate in 640 parts of dry benzene is added dropwise a solution of 172 parts of a sodium dihydro-bis(2-methoxyethoxy)aluminate 70% in benzene, in 160 parts of dry benzene. Upon completion, stirring is continued for 2h.30 at 80° C. The reaction mixture is cooled, poured onto ice-water, alkalized with sodium hydroxide solution and the product is extracted with benzene. The extract is washed twice with water, dried, filtered and evaporated. The residue is converted into the hydrochloride salt in 2-propanol and 1,1'-oxybisethane. The salt is filtered off, boiled in 2-propanol and after cooling, the product is filtered off. It is boiled once more in acetonitrile and the salt is filtered off again after cooling. The free base is liberated in the conventional manner. After extraction with 1,1'-oxybisethane, the latter is washed with water, dried and evaporated, yielding 56.6 parts of 4-(phenylamino)-1-(phenylmethyl)-4-piperidinemethanol as an oily residue.

To a solution of 32 parts of 4-(phenylamino)-1-(phenylmethyl)-4-piperidinemethanol in 90 parts of benzene are added 0.2 parts of N,N,N-triethylbenzenemethanaminium chloride and 150 parts of a sodium hydroxide solution 60%. After stirring vigourously, there are added dropwise 10.9 parts of dimethylsulfate at a temperature below 30° C. Upon completion, stirring is continued at room temperature, first for 2h.30 and further, after the addition of a second portion of 2.6 parts of dimethyl sulfate, for 1h.30. The reaction mixture is cooled in ice-water and 200 parts of water are added. The organic phase is separated and the aqueous phase is extracted with benzene. The combined organic phases are washed with water, dried, filtered and evaporated. The residue is purified by column-chromatography over silica gel using a mixture of trichloromethane and 3% of methanol, saturated with ammonia, as eluent. The pure fractions are collected and the eluent is evaporated, yielding 24.8 parts of 4-(methoxymethyl)-N-phenyl-1-(phenylmethyl)-4-piperidinamine as a residue.

A mixture of 10 parts of 4-(methoxymethyl)-N-phenyl-1-(phenylmethyl)-4-piperidinamine and 200 parts of acetic acid is hydrogenated at normal pressure and at room temperature with 2 parts of palladium-on-charcoal catalyst 10%. After the calculated amount of hydrogen is taken up, the catalyst is filtered off and the filtrate is evaporated. The oily residue is dissolved in water, cooled and alkalized with ammonium hydroxide. The product is extracted with trichloromethane. The extract is washed with water, dried, filtered and evaporated. The oily residue is purified by column-chromatography over silica gel using a mixture of trichloromethane and methanol (90:10 by volume) saturated with gaseous ammonia, as eluent. The pure fractions are collected and the eluent is evaporated, yielding 4.5 parts of 4-(methoxymethyl)-N-phenyl-4-piperidinamine as an oily residue.

A mixture of 10 parts of 2-bromopropane, 9 parts of 4-(methoxymethyl)-N-phenyl-4-piperidinamine, 4.9 parts of N,N-diethylethanamine and 72 parts of N,N-dimethylacetamide is stirred and refluxed for 10.25 hours. After cooling, the formed N,N-diethylethanamine hydrobromide is filtered off and the filtrate is diluted with water. The product is extracted with methylbenzene. The extract is washed thoroughly with water, dried, filtered and evaporated. The residue is purified by column-chromatography over silica gel using a mixture of trichloromethane and methanol (90:10) as eluent. The pure fractions are collected and the eluent is evaporated, yielding 5.7 parts (42.6%) of 4-(methoxymethyl)-1-(1-methylethyl)-N-phenyl-4-piperidinamine as an oily residue.

To a stirred mixture of 5.5 parts of 4-(methoxymethyl)-1-(1-methylethyl)-N-phenyl-4-piperidinamine in 56 parts of benzene is added dropwise a solution of 13.8 parts of benzeneacetyl chloride in 45 parts of benzene at 26°–32° C. Upon completion, stirring is continued first for one hour at 26°–32° C. and further for 3.60 hours at 38°–55° C. After cooling, the precipitated product is filtered off and converted into the hydrochloride salt in a mixture of 2-propanol and 2-propanone (5:1 by volume). The salt is filtered off and dissolved in absolute ethanol. After standing for 72 hours at room temperature, the precipitated product is filtered off, washed with a small amount of 2-propanone and dried, yielding 1.05 parts of N-[4-(methoxymethyl)-1-(1-methylethyl)-4-piperidinyl]-N-phenylbenzeneacetamide hydrochloride; mp. 249.1° C.

EXAMPLE LVIII

By repeating the procedure of steps 1 through 4 of Example LVII and by using an equivalent amount of an appropriate di(lower alkyl) sulfate in step 5 thereof the following intermediates are prepared from the appropriate starting materials:

4-(methoxymethyl)-N-(3-methylphenyl)-1-(phenylmethyl)-4-piperidinamine;
4-(methoxymethyl)-N-(4-methylphenyl)-1-(phenylmethyl)-4-piperidinamine;
4-(methoxymethyl)-N-(2-methylphenyl)-1-(phenylmethyl)-4-piperidinamine;
N-(4-fluorophenyl)-4-(methoxymethyl)-1-(phenylmethyl)-4-piperidinamine;
4-(ethoxymethyl)-N-phenyl-1-(phenylmethyl)-4-piperidinamine; and
4-(ethoxymethyl)-N-(4-fluorophenyl)-1-(phenylmethyl)-4-piperidinamine.

EXAMPLE LIX

Following the procedure of step 7 of Example LVII and using therein equivalent amounts of respectively an appropriate N-aryl-4-(lower alkyloxymethyl)-1-(phenylmethyl)-4-piperidinamine and an appropriate arylacetyl chloride as starting materials the following intermediate products are prepared:

N-[4-(methoxymethyl)-1-(phenylmethyl)-4-piperidinyl]-N-phenylbenzeneacetamide;
N-[4-(methoxymethyl)-1-(phenylmethyl)-4-piperidinyl]-N-(3-methylphenyl)benzeneacetamide;
N-[4-(methoxymethyl)-1-(phenylmethyl)-4-piperidinyl]-N-(4-methylphenyl)benzeneacetamide;
N-[4-(methoxymethyl)-1-(phenylmethyl)-4-piperidinyl]-N-(2-methylphenyl)benzeneacetamide;
N-(4-fluorophenyl)-N-[4-(methoxymethyl)-1-(phenylmethyl)-4-piperidinyl]benzeneacetamide;
N-[4-(ethoxymethyl)-1-(phenylmethyl)-4-piperidinyl]-N-phenylbenzeneacetamide;
N-[4-(ethoxymethyl)-1-(phenylmethyl)-4-piperidinyl]-N-(4-fluorophenyl)-benzeneacetamide;
N-[4-(methoxymethyl)-1-(phenylmethyl)-4-piperidinyl]-N-phenyl-4-methylbenzeneacetamide;
N-[4-(methoxymethyl)-1-(phenylmethyl)-4-piperidinyl]-N-phenyl-4-methoxybenzeneacetamide; and
N-[4-(methoxymethyl)-1-(phenylmethyl)-4-piperidinyl]-N-phenyl-2-thiopheneacetamide.

EXAMPLE LX

Following the procedure of step 5 of Example LVII the following compounds are prepared starting from the appropriate phenylmethyl substituted precursors:

N-[4-(methoxymethyl)-4-piperidinyl]-N-phenylbenzeneacetamide;
N-[4-(methoxymethyl)-4-piperidinyl]-N-(3-methylphenyl)benzeneacetamide;
N-[4-(methoxymethyl)-4-piperidinyl]-N-(4-methylphenyl)benzeneacetamide;
N-[4-(methoxymethyl)-4-piperidinyl]-N-(2-methylphenyl)benzeneacetamide;
N-(4-fluorophenyl)-N-[4-(methoxymethyl)-4-piperidinyl]benzeneacetamide;
N-[4-(ethoxymethyl)-4-piperidinyl]-N-phenylbenzeneacetamide; N-[4-(ethoxymethyl)-4-piperidinyl]-N-(4-fluorophenyl)benzeneacetamide;
N-[4-(methoxymethyl)-4-piperidinyl]-N-phenyl-4-methylbenzeneacetamide;
N-[4-(methoxymethyl)-4-piperidinyl]-N-phenyl-4-methoxybenzeneacetamide; and
N-[4-(methoxymethyl)-4-piperidinyl]-N-phenyl-2-thiopheneacetamide.

EXAMPLE LXI

To a stirred mixture of 7.5 parts of N-(4-chlorophenyl)-1-(1-methylethyl)-4-piperidinamine and 80 parts of 4-methyl-2-pentanone are added dropwise 9 parts of [4-(2-chloro-2-oxoethyl)phenyl] ethyl carbonate. Upon completion, the whole is heated to reflux and stirring is continued for one hour at reflux temperature. After cooling, the precipitated product is filtered off and stirred for 30 minutes in a mixture of alkaline water and trichloromethane. The layers are separated. The organic phase is dried, filtered and evaporated. The oily residue is purified by column-chromatography over silica gel using a mixture of trichloromethane and methanol (90:10 by volume) as eluent. The pure fractions are collected and the eluent is evaporated, yielding 5.5 parts of {4-[2-{(4chlorophenyl)-[1-(1-methylethyl)-4-piperidinyl]amino}-2-oxoethyl]phenyl} ethyl carbonate as an oily residue.

A mixture of 5.5 parts of {4-[2-{(4-chlorophenyl)[1-(1-methylethyl)-4-piperidinyl]amino}-2-oxoethyl]-phenyl}ethyl carbonate and 50parts of a sodium hydroxide solution 10% is stirred for 90 minutes at 45° C. The reaction mixture is cooled to room temperature and acidified with acetic acid to pH 5.5–6. The product is extracted with trichloromethane. The extract is dried, filtered and evaporated. The oily residue is purified by column-chromatography over silica gel using a mixture of trichloromethane and methanol (80:20 by volume) as eluent. The pure fractions are collected and the eluent is evaporated. The oily residue is converted into the hydrochloride salt in 4-methyl-2-pentanone. The salt is filtered off and dried in vacuo for 12 hours at 60° C., yielding 1.9 parts of N-(4-chlorophenyl)-4-hydroxy-N-[1-(1-methylethyl)-4-piperidinyl]benzeneacetamide monohydrochloride; mp. 242.9° C.

We claim:

1. A chemical compound selected from the group consisting of an N-aryl-N-(4-piperidinyl)arylacetamide having the formula:

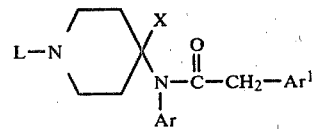

and the pharmaceutically acceptable acid addition salts thereof, wherein:

L is a member selected from the group consisting of hydrogen, cycloalkyl-lower alkyl and lower alkenyl, said cycloalkyl having 3 to 6 carbon atoms;
Ar is a member selected from the group consisting of pyridinyl and 2-pyrimidinyl;
Ar¹ is a member selected from the group consisting of phenyl, mono- and di-substituted phenyl, wherein each substituent in said mono- and di-substituted phenyl is independently selected from the group consisting of halo, lower alkyl, hydroxy and lower alkyloxy; and X is a member selected from the group consisting of hydrogen, lower alkyloxycarbonyl and lower alkyloxymethyl.

2. A pharmaceutical composition comprising an inert carrier material and as an active ingredient an effective anti-arrhythmic amount of a chemical compound selected from the group consisting of an N-aryl-N-(4-piperidinyl)arylacetamide having the formula:

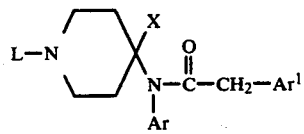

and the pharmaceutically acceptable acid addition salts thereof,
wherein:
- L is a member selected from the group consisting of hydrogen, cycloalkyllower alkyl and lower alkenyl, said cycloalkyl having 3 to 6 carbon atoms;
- Ar is a member selected from the group consisting of pyridinyl and 2-pyrimidinyl;
- $Ar^1$ is a member selected from the group consisting of phenyl, mono- and di-substituted phenyl, wherein each substituent in said mono- and di-substituted phenyl is independently selected from the group consisting of halo, lower alkyl, hydroxy and lower alkyloxy; and
- X is a member selected from the group consisting of hydrogen, lower alkyloxycarbonyl and lower alkyloxymethyl.

3. A method of treating cardiac arrhythmia which comprises the systemic administration to warm-blooded animals of an effective anti-arrhythmic amount of a chemical compound selected from the group consisting of an N-aryl-N-(4-piperidinyl)arylacetamide having the formula:

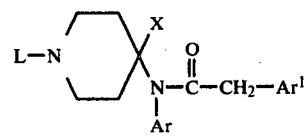

and the pharmaceutically acceptable acid addition salts thereof, wherein:
- L is a member selected from the group consisting of hydrogen, cycloalkyllower alkyl and lower alkenyl, said cycloalkyl having 3 to 6 carbon atoms;
- Ar is a member selected from the group consisting of pyridinyl and 2-pyrimidinyl;
- $Ar^1$ is a member selected from the group consisting of phenyl, mono- and di-substituted phenyl wherein each substitutent in said mono- and di-substituted phenyl is independently selected from the group consisting of halo, lower alkyl, hydroxy and lower alkyloxy; and
- X is a member selected from the group consisting of hydrogen, lower alkyloxycarbonyl and lower alkyloxymethyl.

* * * * *